(12) United States Patent
Benedek et al.

(10) Patent No.: US 10,933,158 B2
(45) Date of Patent: Mar. 2, 2021

(54) AIR TREATMENT SYSTEM AND METHOD OF USE

(71) Applicant: BLUEZONE IP HOLDING LLC, Woburn, MA (US)

(72) Inventors: Karen Benedek, Winchester, MA (US); Philip C. Carbone, North Reading, MA (US); Peter J. Loftus, Cambridge, MA (US); Anna Cheimets, Medford, MA (US); David Hensel, Boston, MA (US)

(73) Assignee: Bluezone IP Holding LLC, Woburn, MA (US)

( * ) Notice: Subject to any disclaimer, the term of this patent is extended or adjusted under 35 U.S.C. 154(b) by 0 days.

(21) Appl. No.: 16/268,128

(22) Filed: Feb. 5, 2019

(65) Prior Publication Data

US 2019/0240370 A1    Aug. 8, 2019

Related U.S. Application Data

(63) Continuation-in-part of application No. 15/878,598, filed on Jan. 24, 2018, which is a continuation-in-part (Continued)

(51) Int. Cl.
*A61L 9/20* (2006.01)
*A61L 9/12* (2006.01)
(Continued)

(52) U.S. Cl.
CPC .............. *A61L 9/205* (2013.01); *A61L 9/014* (2013.01); *A61L 9/046* (2013.01); *A61L 9/122* (2013.01);
(Continued)

(58) Field of Classification Search
CPC . A61L 9/014; A61L 9/046; A61L 9/12; A61L 9/20; A61L 9/205; A61L 2209/14;
(Continued)

(56) References Cited

U.S. PATENT DOCUMENTS 2,628,083 A    2/1953   Rense
3,071,828 A    1/1963   Cornell, Jr.
(Continued)

FOREIGN PATENT DOCUMENTS

DE    36 37 702 A1    5/1988
EP    0 269 941 A1    6/1988
(Continued)

OTHER PUBLICATIONS

EPO, Rijswijk, NL, Form PCT/ISA/210, English language version of International Search Report for Int'l Appln PCT/US2019/016664, dated Jun. 26, 2019 (5 pages).
(Continued)

*Primary Examiner* — Timothy C Cleveland
(74) *Attorney, Agent, or Firm* — Wolf, Greenfield & Sacks, P.C.

(57) ABSTRACT

A built-in apparatus and method for treating air including a housing with an air inlet and an air outlet. An air mover positioned near the air outlet is configured to draw the air through the air inlet. The housing encloses an air treatment zone, such as including an oxidizing zone, and an ozone removal zone positioned downstream of the air treatment zone and oxidizing zone. The air treatment zone includes UV light and/or ozone that partially oxidizes the chemical contaminants in the air treatment zone. A catalyst in the oxidizing zone oxidizes elements within the air treatment zone. The ozone removal zone includes a second, different catalyst material. A UV bulb that may or may not generate ozone is positioned within or downstream of the first and/or
(Continued)

second catalyst materials to assist catalyst oxidation and/or self-clean the apparatus.

23 Claims, 13 Drawing Sheets

Related U.S. Application Data of application No. 15/461,433, filed on Mar. 16, 2017, now abandoned.

(60) Provisional application No. 62/626,548, filed on Feb. 5, 2018.

(51) Int. Cl.
| | | |
|---|---|---|
| *A61L 9/014* | (2006.01) | |
| *B01J 23/34* | (2006.01) | |
| *B01J 35/00* | (2006.01) | |
| *B01D 53/00* | (2006.01) | |
| *B01D 53/86* | (2006.01) | |
| *A61L 9/04* | (2006.01) | |
| *F24C 15/20* | (2006.01) | |
| *B60H 3/00* | (2006.01) | |

(52) U.S. Cl.
CPC .............. *A61L 9/20* (2013.01); *B01D 53/007* (2013.01); *B01D 53/869* (2013.01); *B01D 53/8675* (2013.01); *B01D 53/8678* (2013.01); *B01D 53/8687* (2013.01); *B01J 23/34* (2013.01); *B01J 35/004* (2013.01); *B60H 3/0071* (2013.01); *F24C 15/205* (2013.01); *A61L 2209/111* (2013.01); *A61L 2209/12* (2013.01); *A61L 2209/134* (2013.01); *A61L 2209/14* (2013.01); *A61L 2209/16* (2013.01); *A61L 2209/212* (2013.01); *A61L 2209/22* (2013.01); *B01D 2251/104* (2013.01); *B01D 2255/2073* (2013.01); *B01D 2255/802* (2013.01); *B01D 2255/9032* (2013.01); *B01D 2257/106* (2013.01); *B01D 2257/708* (2013.01); *B01D 2257/90* (2013.01); *B01D 2257/91* (2013.01); *B01D 2258/0275* (2013.01); *B01D 2258/06* (2013.01); *B01D 2259/4508* (2013.01); *B01D 2259/804* (2013.01)

(58) Field of Classification Search
CPC ........... A61L 2209/16; A61L 2209/212; A61L 2209/22; B01D 46/0038; B01D 53/007; B01D 53/8675; B01D 53/8678; B01D 53/869; B01D 2251/104; B01D 2255/2073; B01D 2255/9032; B01D 2259/804; F24C 15/205

See application file for complete search history.

(56) References Cited

U.S. PATENT DOCUMENTS

| | | | |
|---|---|---|---|
| 3,744,216 A | 7/1973 | Halloran | |
| 4,210,429 A | 7/1980 | Golstein | |
| 4,302,677 A | 11/1981 | Albertsson et al. | |
| 4,343,765 A | 8/1982 | Elston et al. | |
| 4,904,289 A | 2/1990 | Miyakami et al. | |
| 4,990,311 A | 2/1991 | Hirai et al. | |
| 5,015,442 A | 5/1991 | Hirai | |
| 5,029,252 A | 7/1991 | Ameseder | |
| 5,152,077 A | 10/1992 | Liang | |
| 5,230,220 A | 7/1993 | Kang et al. | |
| 5,262,130 A | 11/1993 | Kissel et al. | |
| 5,326,539 A | 7/1994 | Taylor | |
| 5,369,892 A | 12/1994 | Dhaemers | |
| 5,472,676 A * | 12/1995 | Terui .................. | B01D 53/8675 423/219 |
| 5,505,904 A | 4/1996 | Haidinger et al. | |
| 5,523,057 A | 6/1996 | Mazilli | |
| 5,601,786 A | 2/1997 | Monagan | |
| 5,788,930 A | 8/1998 | McMurray | |
| 5,853,457 A | 12/1998 | Eysmondt et al. | |
| 5,925,320 A | 7/1999 | Jones | |
| 6,093,237 A | 7/2000 | Keller et al. | |
| 6,134,806 A | 10/2000 | Dhaemers | |
| 6,391,272 B1 | 5/2002 | Schroeder | |
| 6,500,387 B1 * | 12/2002 | Bigelow .................. | A61L 9/20 250/432 R |
| 6,613,277 B1 | 9/2003 | Monagan | |
| 6,845,569 B1 | 1/2005 | Kim | |
| 6,893,610 B1 | 5/2005 | Barnes | |
| 7,651,555 B2 | 1/2010 | Roseberry et al. | |
| 8,003,058 B2 * | 8/2011 | Bergeron ................ | A61L 9/205 422/186.04 |
| 8,114,358 B2 | 2/2012 | Benedek et al. | |
| 8,388,900 B2 | 3/2013 | Benedek et al. | |
| 2002/0031460 A1 | 3/2002 | Kulp | |
| 2002/0098109 A1 | 7/2002 | Nelson et al. | |
| 2002/0139124 A1 | 10/2002 | Palermo | |
| 2003/0206840 A1 | 11/2003 | Taylor et al. | |
| 2004/0003511 A1 | 1/2004 | Silver | |
| 2004/0120845 A1 | 6/2004 | Potember et al. | |
| 2004/0146437 A1 | 7/2004 | Arts et al. | |
| 2004/0161371 A1 | 8/2004 | Russell et al. | |
| 2004/0170537 A1 | 9/2004 | Hara | |
| 2005/0069465 A1 | 3/2005 | McEllen | |
| 2005/0175498 A1 | 4/2005 | Oke | |
| 2005/0129589 A1 | 6/2005 | Wei et al. | |
| 2005/0129591 A1 | 6/2005 | Wei et al. | |
| 2005/0186108 A1 | 8/2005 | Fields | |
| 2006/0032199 A1 | 2/2006 | Beam et al. | |
| 2006/0104858 A1 | 5/2006 | Potember et al. | |
| 2007/0253860 A1 | 11/2007 | Schroder | |
| 2008/0118395 A1 | 5/2008 | Benedek | |
| 2009/0041632 A1 | 2/2009 | Day et al. | |
| 2010/0054989 A1 | 3/2010 | Benedek et al. | |
| 2010/0158749 A1 | 6/2010 | Benedek et al. | |
| 2012/0244036 A1 | 9/2012 | Benedek et al. | |
| 2013/0256560 A1 | 10/2013 | Yerby | |
| 2013/0287626 A1 | 10/2013 | Benedek et al. | |
| 2014/0193296 A1 | 7/2014 | Jurak et al. | |
| 2015/0224218 A1 * | 8/2015 | Burnett .................. | A61L 9/22 422/105 |
| 2017/0246333 A1 | 8/2017 | Carbone et al. | |
| 2018/0264157 A1 | 9/2018 | Benedek et al. | |
| 2018/0264160 A1 | 9/2018 | Benedek et al. | |
| 2019/0240371 A1 | 8/2019 | Benedek et al. | |

FOREIGN PATENT DOCUMENTS

| | | |
|---|---|---|
| JP | 2002-263181 A | 9/2002 |
| JP | 2005-226861 A | 8/2005 |
| KR | 2008 0039643 | 5/2008 |
| KR | 10-2010-0058087 A | 6/2010 |
| WO | WO 90/02572 A1 | 3/1990 |
| WO | WO 03/080375 A1 | 10/2003 |
| WO | WO 2008/103719 A1 | 8/2008 |
| WO | WO 2008/127315 A2 | 10/2008 |
| WO | WO 2016/080903 A1 | 5/2016 |

OTHER PUBLICATIONS

EPO, Rijswijk, NL, Form PCT/ISA/237, Written Opinion of the International Searching Authority for Int'l Appln PCT/US2019/016664, dated Jun. 26, 2019 (8 pages).

Co-pending Divisional U.S. Appl. No. 16/115,336, "Air Treatment System," filed Aug. 28, 2018.

* cited by examiner

| Element | Config.A | Config.B | Config.C | Config.D | Config.E | Config.F | Config.G | Config.H | Config.I |
|---|---|---|---|---|---|---|---|---|---|
| Ozone (bulb/CD) | ✓ | ✓ | ✓ | | | | | ✓ | ✓ or ✓ |
| UV (bulb/LED) | ✓ | ✓ | ✓ | ✓ | ✓ | ✓ | ✓ | ✓ | |
| Prefilter | ✓ | ✓ | ✓ | ✓ | ✓ | ✓ | ✓ | | |
| Filter | ✓ | ✓ | | | | | | | |
| Heater | | | | | | | | ✓ | |
| Catalyst 1 | ✓ | ✓ | ✓ | ✓ | ✓ | ✓✓ | ✓✓ | ✓ | ✓ |
| Catalyst 2 | ✓ | ✓ | ✓ | ✓✓ | ✓✓ | ✓✓ | ✓✓ | ✓ | ✓ |
| | Broad VOC and PM and Germicidal UV PLUS Self clean<br><br>Bulbs | Broad VOC and PM and Antimicrobial PLUS Self clean<br><br>No Mercury Bulbs | Broad VOC and Antimicrobial<br><br>No PM filter or prefilter<br><br>Bulbs | Broad VOC High Capacity Antimicrobial<br><br>No PM filter or prefilter<br><br>No Mercury Bulbs | Broad VOC High Capacity and PM and Germicidal UV and self Clean<br><br>Bulbs and CD | Same as A plus higher capacity and longer life | Same as B plus higher capacity and longer life | All VOC and PM and Antimicrobial and Self clean plus heat and higher performance<br>Bulbs | Broad VOC and Antimicrobial<br><br>No PM/ No filter<br><br>Ozone bulb or corona discharge |

✓✓ means additional catalyst volume

FIG. 11A

| Element | Config.J | Config.K | Config.L | Config.M | Config.N | Config.O | Config.P | Config.Q | Config.R |
|---|---|---|---|---|---|---|---|---|---|
| Ozone (bulb/CD) | | | | | | | | | |
| UV (bulb/LED) | ✓ | ✓ | | | | | ✓ | ✓ | ✓ |
| Prefilter | ✓ | ✓ | | | | | | | |
| Filter | | | ✓ | ✓ | | | ✓ | ✓ | |
| Heater | | | ✓ | ✓ | ✓ | ✓ | | | |
| Adsorber/Carbon | | | | | | | ✓ | | Coated on filter |
| Catalyst 1 | | ✓ | ✓ | ✓ | ✓ | | ✓ | Coated on filter | ✓ |
| Catalyst 2 | ✓ | ✓ | ✓ | | ✓ | ✓✓ | | | |
| | Targeted VOC Prefilter PM Filter | Multiple Targeted VOC Prefilter PM Filter | Multiple Targeted VOC Self clean from heater | Targeted VOC and PM with clean from heater | Targeted VOC self clean from heater | Targeted high capacity VOC Self clean from heater | HCHO removal Microbial kill Residual odor removal | Catalyst serviced with filter | Odor removal filter and catalyst |

✓✓ means additional catalyst volume

FIG. 11B

AIR TREATMENT SYSTEM AND METHOD OF USE

CROSS REFERENCE TO RELATED APPLICATIONS

This application is a Continuation-In-Part of U.S. patent application Ser. No. 15/878,598, filed 24 Jan. 2018, which is a Continuation-In-Part of U.S. patent application Ser. No. 15/461,433, filed 16 Mar. 2017. This application also claims the benefit of U.S. Provisional Patent Application Ser. No. 62/626,548, filed on 5 Feb. 2018. The parent and provisional patent applications are hereby incorporated by reference herein in their entirety and are made a part hereof, including but not limited to those portions which specifically appear hereinafter.

BACKGROUND OF THE INVENTION

Field of the Invention

The subject matter described herein relates generally to cleaning air, and more specifically to built-in air cleaning systems that treat air by removing one or more impurities from the air and are controlled with inputs from the operation of components and systems in the built-in environment.

In one aspect, the subject matter disclosed herein relates to a system of modular and interchangeable methods and assemblies for treating an atmosphere to remove impurities. Such impurity removal may involve one or more of a treatment to sanitize, filter, decontaminate, deodorize, purify, condition, heat, humidify, and/or dry the atmosphere, for example. Such methods and assemblies may employ a particulate filter to remove aerosols and particulate matter, germicidal UV light at wavelengths between 200 and 300 nm to inactivate micro-organisms, ozone generation to oxidize chemical contaminants, the ozone in conjunction with UV light to more rapidly oxidize impurities in the air, an oxidizing catalyst to convert chemical compounds in the air into less harmful constituents, a catalytic decomposer to destroy ozone, UV light to promote more complete mineralization of VOCs across a low temperature oxidizing catalyst, ozone to promote more complete mineralization of VOCs across the low temperature catalyst, and a fan or other air mover to draw air through the system. In one aspect of the invention, the materials, apparatuses and assemblies are integrated into an air cleaning product that is built into a residential kitchen and/or is connected electronically to a range and a ventilation hood in order to better manage the grease and odors that are created from the cooking process. In another aspect of the invention, the air cleaning product is integrated into and/or within an automobile where it is connected electronically to the remote starter, automobile cabin temperature sensor, and/or air conditioning system to remove VOCs that evolve from the cabin materials. In another aspect of the invention, the air cleaning product is built into a refrigerator and/or connected electronically to a door switch, an internal temperature sensor, and/or an evaporator fan to remove odors and VOCs from the food storage compartment.

Discussion of Related Art

Residential, commercial, industrial, and/or automotive spaces can have atmospheres that are contaminated with odors, gases, volatile organic compounds, volatile inorganic compounds, microbes, particulate matter and/or allergens that cause discomfort or health hazards to people occupying those spaces. Conventional air cleaning technologies filter the air with materials that trap or otherwise adsorb or absorb gases, odors, microbes and/or allergens. These trapped or otherwise held contaminants are always present in the filters and can be re-emitted into the atmosphere. Activated carbon is typically used to capture odors and/or volatile compounds from the air. It is well known that activated carbon captures more contaminants when the contaminant concentration in the environment is high. When the contaminant concentration falls, the gases begin to desorb from the activated carbon and exhaust or flow back into the air. While this is not useful to completely remove the contaminants from the air, it is a way to make flow of contaminants into an improved air treatment system more stable when the concentration in the environment is rapidly changing. One preferred air cleaning approach would be to convert the odors, gases and/or volatile organic compounds into harmless compounds that are not noticed by or cause harm to occupants in the room. It is also preferable for an air purifier to inactivate microbes and/or alter allergens in a way that renders them harmless rather than to capture the particles without altering their properties. It is also desirable to have an air purifier that offers a self-clean cycle that deodorizes, oxidizes or otherwise cleans its internal components of or from captured pollutants that cause odors, or can reproduce and grow over time (such as microbes) or that could decrease the performance of the components that are removing the pollutants from the air. That way, there is less need to replace filters that are filled with particulates and other contaminants that can be re-emitted into the atmosphere.

There is a need for an alternative approach to air cleaning that would convert or inactivate rather than capture gaseous contaminants in the atmosphere. There is also a need to ensure that the contaminants that are converted by the system are fully oxidized and do not produce significant secondary contaminants. There is also a need for an alternative approach to air cleaning that incorporates a self-clean function to deodorize and sanitize the filters that capture aerosols. There is a need for a catalyst containing air cleaning system to periodically refresh the catalyst so that its performance is maintained over time. There is a need for the various components of an air cleaning system to be modular so that the manufacturer has a cost-effective way of creating a suite of products that preferentially clean one type of pollutant or another, or that are offered to the market at different price points with different air cleaning capabilities.

There is a need for an air cleaning system that cleans cooking odors from a room such as a kitchen or combined kitchen and/or dining room. This cooking odor removal system could beneficially be configured as a built-in appliance that has a set operating cycle tied to the operation of the cooktop and the ventilation hood. With a built-in system, the air cleaner could be connected electronically to the cooktop and the ventilation hood such that the ventilation hood operates when the cooktop is powered or energized. When cooking is over or complete and the cooktop power is shut off, the ventilation hood fan could be shut down and the air cleaner could be turned on. The air cleaner could then begin an air cleaning cycle that removes residual odors and aerosols of grease or oils, for example, in the air in the kitchen. This air cleaning cycle could be customized based on the size of the kitchen, for example.

There is a need for an air cleaning system that could be built into an automobile and operated in conjunction with other automobile systems or characteristics, such as the internal temperature or the operation of the air conditioning system. An air cleaner built into an automobile could be activated by the remote starting fob, and/or mobile telephone, for example, so that the air begins to be cleaned before the occupant enters the car. An air cleaning system built into a car could be activated when the temperature in the car exceeds a threshold that could lead to excessive generation of VOCs from the materials in the cabin. This automobile air cleaning system could be activated or deactivated as appropriate when the air conditioning and ventilation system of the car are operating.

There is a need for an air cleaning system to be built into a refrigerator so that it cleans the air in the refrigerator in response to certain conditions of the refrigerator, such as turning off when the door is opened, or turning on after the door has been subsequently closed, for example, after new foods have been added to the refrigerator. The air cleaning device could be operated preferentially during certain cooling cycles or conditions, such as when the internal evaporator fan is operating and/or when the compressor is not operating.

SUMMARY OF THE INVENTION

It is an object of the subject matter disclosed herein to provide an improved method and/or apparatus for treating an atmosphere containing pollutants such as chemical contaminants, volatile organic compounds, odors, aerosols, particulate matter, allergens, pollen, volatile inorganic compounds and/or other airborne compounds that are unhealthy, unwanted or unpleasant.

Also provided are a method and device to generate, use, and ultimately at least partially destroy the generated ozone for decontamination, deodorization, and/or conditioning of the air and/or the materials. The air cleaning unit can be positioned inside a space of various suitable configurations or designs. Air that requires treatment is drawn from the space into the cleaning unit, passes across an ozone generator, such as a UV bulb that emits light rays in the UV wavelength that generates ozone, or a corona discharge unit that creates ozone from a voltage difference across a gap. In one embodiment it has been found that the combination of ozone and UV light serve to rapidly destroy contaminants within the cleaning unit. The clean air is then drawn across a catalyst to dissociate ozone to molecular oxygen. Clean, ozone-free air is then reintroduced to the chamber or surrounding space.

Also provided are a method and device to oxidize volatile gaseous compounds, odors, and molecular contaminants in three steps. In the first step, certain molecules are partially broken down by ozone in the presence of UV light. These products of the reaction between the contaminants and ozone in the presence of UV light may be smaller hydrocarbons or other molecules that have been transformed in some way from their original chemical structure. The products of the reaction may be partially or fully oxidized compounds. In a second step, these transformed molecules are then passed through an oxidizing catalyst that can further oxidize or completely mineralize the transformed chemicals. In this method, air that requires treatment is drawn from the chamber into the cleaning unit, and passes across an ozone generator, such as a UV bulb that emits light rays in the UV wavelength that generates ozone, or a corona discharge unit.

The invention provides an apparatus for treating air that includes a housing with an air inlet and an air outlet. The housing encloses an air treatment zone and an ozone removal zone, wherein the ozone removal zone is positioned downstream of the air treatment zone with respect to a flow direction of the air being treated. A first catalyst layer extends across the air treatment zone and includes a first catalyst material. A second catalyst layer extends across the ozone removal zone and is spaced apart from the first catalyst layer. The second catalyst layer includes a second catalyst material that is different from the first catalyst material, wherein the first catalyst material oxidizes organic and/or inorganic compounds, and the second catalyst material removes ozone. Embodiments of this invention include an ozone generator and/or an ultraviolet source disposed upstream of, downstream of, or within the first catalyst layer.

As an example, a first ozone generator and/or an ultraviolet source is downstream of the first catalyst layer, and is configured to promote oxidation of chemical contaminants via a first catalyst material and/or to clean the first catalyst layer. A second ozone generator and/or ultraviolet source can be disposed upstream of the first catalyst layer. The first ozone generator and/or ultraviolet source can also be downstream of the second catalyst layer and a further catalyst layer can be downstream of the first ozone generator and/or an ultraviolet source, wherein the further catalyst layer comprises the first catalyst material or the second catalyst material.

The invention further includes an apparatus for treating air with an ozone generator within the air treatment zone, a plurality of first catalyst layers each spaced apart from each other and extending across the air treatment zone, and each including a first catalyst material, and a plurality of second catalyst layers extending across the ozone removal zone, each spaced apart from each other and the first catalyst layers. The second catalyst layers each include a second catalyst material that is different from the first catalyst material, wherein each of the first and second catalyst materials comprises manganese. An ozone and/or ultraviolet source is disposed within an air flow space between the first and second catalyst layers or between the second catalyst layers and a downstream further catalyst layer, wherein the further catalyst layer comprises the first catalyst material or the second catalyst material.

The invention further includes a method for treating air including: partially oxidizing chemical contaminants via application of ozone and/or ultraviolet light; oxidizing the chemical contaminants via a first catalyst material downstream of the application of ozone and/or ultraviolet light; and removing ozone via a second catalyst material downstream of the first catalyst material. The method can further include applying further ozone and/or ultraviolet light downstream of or within (e.g., downstream of the first catalyst inlet or sheet) the first catalyst material, and/or downstream of or within the second catalyst material. The downstream application can assist in increasing an oxidation rate of the chemical contaminants throughout a layer of the first catalyst material. The method can further include altering a rate at which the chemical contaminants enter a layer of the first catalyst material via a layer of adsorbent material upstream of the layer of the first catalyst material.

Embodiments of this invention further include a method for treating air including the steps of: providing or forming an air treatment zone in a housing downstream of a housing inlet; partially oxidizing chemical contaminants via a first application of ozone and/or ultraviolet light within the air treatment zone; further oxidizing the chemical contaminants through a first catalyst layer including a first catalyst material, downstream of the application of ozone and/or ultraviolet light; removing ozone through a second catalyst layer including a second catalyst material downstream of the first catalyst layer; and applying further ozone and/or ultraviolet light downstream of the first and/or second catalyst material layer. The further ultraviolet light can additionally or alternatively be adapted to clean the first catalyst layer and/or the second catalyst layer.

In embodiments of this invention, it has been found that the combination of ozone and UV light serves to rapidly oxidize contaminants within the cleaning unit. The UV light can be generated by the UV bulb that generates the ozone (wavelengths less than 200 nm), or by a second UV bulb generating light at wavelengths in the UVC spectrum (wavelength 200-300 nm) or by light emitting diodes (LEDs) that emit at UV wavelengths that are 250 nm and longer. The UV light could also be generated by an array of LED sources that individually emit at various wavelengths in the UVA, UVB and UVC spectra. The partially oxidized contaminants are then drawn through a catalyst designed to further oxidize these partially oxidized contaminants.

The ozone and/or UV sources can be used to provide a different self-cleaning mode. The invention further includes steps and configurations for cleaning the first catalyst material by exposing the first catalyst material to ozone at a flow rate lower than used in an air cleaning mode and an ozone concentration higher than used in the air cleaning mode, wherein the cleaning removes chemicals that have been adsorbed on the first catalyst material. The invention includes steps of establishing a predetermined operating cycle including an air cleaning mode and a self-cleaning mode, wherein the operating cycle comprises a first air cleaning time at a first flow rate and a second self-clean time at a reduced flow rate; and operating the further downstream ozone and/or ultraviolet light during the self-cleaning mode.

Catalysts useful in the invention may be specifically formulated to oxidize contaminants at room temperature. A room temperature or relatively low temperature catalyst is one that is formulated to perform at temperatures between 0° and 40° C. Alternatively, a heater in the system could be used in conjunction with a catalyst formulated to operate at elevated temperatures. A catalyst system in the air purifier could contain two catalyst formulations: one catalyst designed to oxidize contaminants such as hydrocarbons, aldehydes, amines, alcohols or other compounds; and the second catalyst designed to dissociate ozone to molecular oxygen. In the third step, the ozone containing air is drawn over the ozone reduction catalyst to remove ozone from the air. A second UV lamp could be used after either catalyst layer to achieve more complete oxidation of the VOCs. Clean, ozone-free air is then emitted from the device and reintroduced to the room.

In some embodiments, in the apparatus for treating air, the device includes a first catalyst section hosting the catalyst, a second catalyst section hosting the different catalyst, and a spacer positioned between the first and the second catalyst sections. In some embodiments of the section holding the catalysts, each catalyst section is comprised of a set of catalyst sheets separated by spacers. These sheets of catalysts may be in the geometry of an expanded metal, a honeycomb, a corrugated sheet, a porous foam and/or other volume with a relatively high surface area that allows air to flow through it. The spacers allow mixing of the air between the catalyst sheets, decreasing the chance that some contaminants in the air travel through the catalyst section untreated. The spacers also can create a region of turbulence at the entrance section of each catalyst layer that enhances reaction rates in the channels of the catalyst.

In some embodiments, the catalysts may be comprised of active materials that oxidize chemical compounds at room temperature. This catalyst may be made of manganese oxides, for example. In some embodiments of this invention, the catalyst comprises manganese dioxide wherein manganese dioxide is a general term and is intended to refer to and include different forms of manganese oxides, including but not limited to cryptomelane, Nsutite, pyrolusite, ramsdellite which is also referred to as alpha-$MnO_2$, beta-$MnO_2$ or R—$MnO_2$ or oxides of manganese with a molar ratio of oxygen to manganese of 1 to 3, for example.

The catalyst may be enhanced by including other elements, such as sodium, cerium, copper, or precious metals to provide higher conversion or more specific conversion of individual impurities, such as volatile organic compounds.

The catalyst material itself may be prepared at different temperatures or using different processes in order to achieve specific performance characteristics. The calcining temperature of the material can impact the surface area of and the number of active sites on the material. The surface area and active sites can impact the relative rates of adsorption and desorption from the catalyst. The differences in rates of adsorption and desorption can impact the relative conversion efficiencies of VOCs and ozone. These differences can also impact the sensitivity of the catalyst to moisture. In this way, two catalysts made of the same chemical materials can have widely different performance levels and different uses. For example, a manganese oxide catalyst prepared in one way can be an excellent low temperature oxidation catalyst. A manganese oxide catalyst prepared in a different way can be an excellent ozone removal catalyst.

The catalyst may be applied to a variety of substrates that provide a useful geometry for the system. The substrate may be a metal honeycomb structure, a metal corrugated structure, a ceramic corrugated structure, an extruded ceramic structure and/or an expanded metal structure.

In some embodiments, the catalyst is designed to resist the adsorption of water into the active sites of the catalyst. The adsorption of water can decrease the effectiveness with which catalysts convert ozone to oxygen. Hydrophobic compounds such as siloxanes are added to catalysts to resist the adsorption of water molecules. Alternatively, the pore structure can be altered to allow water to be desorbed from the catalyst material.

The cell density of the support structures can be between 100 and 1000 cells per square inch, with preferable performance of cell densities of the support structures between 350 and 900 cells per square inch. The catalytic activity of the manganese catalyst can be enhanced by positioning UV light to shine into the honeycomb structure. The enhancement of the reaction rate may result from increasing the energy level of an adsorbed gas molecules or from creating various reactive species that cause additional oxidation of the adsorbed VOCs. The catalytic activity of the manganese catalyst may be refreshed by adding ozone between the layers of the oxidizing catalyst in order to maintain an active oxidizing atmosphere throughout the catalyst layers.

It is another object of the subject matter disclosed herein to trap and treat particulate matter or aerosols on or in a filter. This filter may be a high efficiency particle arresting (HEPA) filter or other particle capturing Material that restricts the passage of particles or aerosols through the material. It is desirable to treat the particles on the filter so that the contaminants themselves do not degrade the performance of the filter. It is also desirable to treat the particles so that they are rendered inert and cannot cause harm if the particles come off the filter either in standard use or when replacing the filter. It is desirable to treat the particles on the filter so that they do not emit odors or toxic gases into the atmosphere while attached to and concentrated on the filter. It is desirable to treat any microbial particles so that the microbes cannot reproduce on the filter and sporulate or otherwise regenerate from the filter itself.

It is another object of the subject matter disclosed herein to trap and treat aerosols of grease or oil on a cleanable grease filter that is made of metal screen, expanded metal, and/or other water washable filter. This grease filter could be configured so that a direct exposure to UV light and ozone oxidize the grease off of the filter. The grease filter could also be configured to allow large amounts of grease to flow off the filter into one or more channels specifically designed to contain and direct the grease into a cleanable storage container.

One method of treating the particulate matter on the filter is to expose the filter to ozone in a manner that ensures that the ozone does not exit or discharge the air cleaner and become introduced into the storage chamber or enclosed room or space. One method to clean the filter with ozone is to flow air through the unit and turn on or start an ozone generating device such as a UV bulb that operates below 200 nm wavelength, or by turning on or starting a corona discharge unit. It may be preferable to adjust the air flow to a level that allows the ozone concentration to rise above a threshold level, such as between 300 ppb and 10 ppm. Preferably this concentration may be between 500 ppb and 2 ppm. It may also be preferable to adjust the flow rate so that a catalyst in the system removes the ozone on the downstream side of the filter and operates at a reasonable space velocity, such as less than 200,000 hr-1 or more preferably less than 100,000 hr-1. By adjusting the air flow rate during the self-clean cycle with ozone generation, the particle treatment can be maximized and the system cost can be minimized. This operational limitation will reduce the amount of ozone reduction catalyst needed while producing high enough concentrations of ozone to fully clean the filter of odors and organic materials.

To ensure that the products of oxidation are as fully mineralized as possible, it may be preferable to operate the system at catalyst space velocities that are even lower, such as at 10,000 hr-1. It is another object of the subject matter disclosed herein to provide a self-cleaning function for the internal components of the air purifier, for example, by exposing a filter to UV light while passing or flowing air through the filter at a low, a medium, a high or no flow rate to deodorize and sanitize as well as oxidize material captured on or attached to the filter.

It is another object of the subject matter disclosed herein to provide a self-cleaning function that combines exposure of a particulate filter (e.g., a particle matter filter) to UV light with air flow through the particulate filter to deodorize, sanitize and/or oxidize material captured on a filter or a filter material, preferably but not necessarily in combination with a control cycle that reduces the air flow rate to a low level while exposing the particulate filter to ozone gas and reducing a space velocity of the ozone-containing air through a catalyst downstream of the particulate filter to a level less than 100,000 hr-1, for example.

It is another object of the subject matter disclosed herein to provide a self-cleaning function that cleans the catalyst of adsorbed contaminants that have not been fully reacted and desorbed from the catalyst. This catalyst self-cleaning function is in some embodiments is provided by creating an air flow through the unit and operating the ozone generator to establish an ozone concentration throughout the catalyst that will remove at least a portion of the contaminants on the catalyst that occupy active sites and would otherwise decrease the catalytic performance of the catalyst. When the catalyst is exposed to ozone at a preferable concentration at a preferable space velocity, the ozone will react with the adsorbed chemicals and allow them to be desorbed from the catalyst. Space velocities for this function could be as low as 10,000 hr-1 for example.

In another aspect of this invention, it may be preferable to operate a heater upstream of the catalyst during the self-cleaning mode in order to increase the reaction rate of the ozone with the molecules adsorbed in the surfaces of the catalyst. The higher temperatures increase the reaction rate of the molecules with the ozone and provide a more complete oxidation of the molecule. The higher catalyst temperatures also can increase the desorption rate of the oxidized chemicals off of the surface of the catalyst. The heating of the catalyst can also serve to drive any adsorbed water out of the catalyst, thus increasing its ozone conversion performance. In another aspect of the invention, the heater may surround the exterior of the catalyst to provide heating of the catalytic material with limited or no air flow through the catalyst.

In another aspect of this invention, it may be preferable to operate a UV bulb at a layer downstream of the inlet to the catalyst, shining UV light through the honeycomb to increase the rate of complete oxidation of molecules on active sites on the catalyst. This outlet UV light could be positioned at the outlet of the oxidizing catalyst layers or the ozone removal catalyst layers.

There is also provided a method for at least one of sanitizing, decontaminating, filtering, deodorizing, conditioning and drying an atmosphere exposed to a material within an enclosed space. In accordance with one embodiment, such method involves circulating the atmosphere through an atmosphere treating unit in a primary flow direction. Ozone is generated within the atmosphere treating unit. The generated ozone mixes with the atmosphere in the atmosphere treating unit. The mixture of atmosphere and ozone is exposed to UV light in the atmosphere treating unit to remove at least a portion of the contaminants in the atmosphere. The ozone is removed from the UV light-exposed mixture of atmosphere and ozone to form an ozone-depleted containing an amount of ozone below a preselected threshold amount. The ozone-depleted mixture can then be appropriately exhausted into the enclosed space. In some embodiments of the subject matter disclosed herein, a control system is employed to reverse the flow of the blower or air mover, thereby passing or flowing air containing ozone out of the air treating unit and into the enclosed space. This reversed air flow can be timed or controlled with a sensor in a way to provide a defined dosage of ozone into the enclosed space. Once the dose or dosage is delivered, the flow direction can be reversed again to the primary flow direction so that both the contaminants in the air and the ozone in the air can be removed.

The system of the subject matter disclosed herein, which includes the apparatus and/or the method, can produce ozone to oxidize contaminants and then complete the oxidation of the contaminants across a first oxidizing catalyst and then dissociate the excess ozone back to oxygen across a second ozone removal catalyst in order to maintain appropriate levels of ozone within the enclosed space or storage container. The system of the subject matter disclosed herein provides a number of significant benefits compared to existing technology.

Circulation of air and ozone in the presence of UV light through a well-designed unit can be more efficient at cleaning the air as compared to injecting gaseous ozone, at non-hazardous levels, into still or calm air or other ambient conditions. It appears that at low concentrations of ozone, random encounters with contaminants results in too slow of a process of contaminant removal. The reaction of ozone with ethylene or other organic gases is greatly enhanced in the presence of UV light. However, there can be significant benefits to combining both of these methods to maximize benefits obtained from the use of ozone.

The subject matter disclosed herein provides two opportunities to oxidize the odors and the microorganisms, one in an air cleaning unit, and the second, such as at a lower ozone concentration, in the ambient air of the storage container or room. This dual approach can better remove impurities from the air in the enclosed space and from surfaces of the materials. Ozone concentrations are relatively high in the air cleaning unit and the mixing rates between the ozone and the air is relatively high, and thus the oxidation rates of the impurities is relatively high. The air in the enclosed space or room can be quickly deodorized and sanitized. By establishing the desired control sequence of flow direction through the air treating unit, the concentration of ozone in the enclosed space can be precisely established. A very low concentration of ozone can be established in the enclosed space or room in order to sanitize surfaces of the materials. This dual approach can minimize negative effects of ozone concentrations in the air handling system or the surface of the materials in the room or container.

It is another object of the subject matter disclosed herein to clean the air in a space such as a room in a residential, commercial, or industrial building. The subject matter disclosed herein cleans the air by inactivating, altering and/or converting these contaminants into harmless gases and/or particles. The subject matter disclosed herein is an alternative to filtering or capturing contaminants in a way that requires frequent replacement of filters and allows for the re-emission of these unaltered contaminants back into the atmosphere.

It is another object of the subject matter disclosed herein to provide a self-cleaning function, for example, by exposing a filter to ozone and ultra-violet wavelength light to deodorize and sanitize as well as oxidize material captured on the filter and/or by exposing the catalyst to ozone, UV light, and/or heat to clean/refresh the catalyst from adsorption of organic compounds.

It is another object of the subject matter disclosed herein to clean the air, such as in or within an automobile. The assembly and method can be used to treat air in an automobile, where contaminants may be generated from the interior cabin materials of the car, i.e., VOC emissions from the plastics and glues and stabilizers and leather. Contaminants in the air of an automobile cabin may also come through the ventilation system or through the windows from outside the car where pollution levels may be high. Pollutants outside a car may include particulate matter, ozone, carbon monoxide, soot, VOCs, and other chemicals.

In accordance with the disclosed subject matter, apparatuses, systems, and methods are described for treating impurities in air and materials.

Disclosed subject matter includes, in one aspect, an apparatus for treating air, which includes a housing with an air inlet and an air outlet, the housing enclosing an air treatment zone comprised of multiple elements that can be used in various combinations depending on the contaminants being cleaned from the air. The elements are designed in a way to be included or excluded from a product assembly, making a modular air cleaning device that can be configured by the manufacturer to address one or more contaminants in a cost effective manner. The modular sections include an air inlet section with a baffle to prevent light of any type, including ultraviolet light, from exiting the unit through the air inlet area. The modular sections may also include a volume that contains an ultraviolet light. The ultraviolet light can be of a germicidal wavelength, an ozone generating wavelength, and/or a wavelength that breaks down specific materials and contaminants.

The ultraviolet light may be produced by a mercury vapor lamp that emits a UV wavelength below 200 nm, with most of the emission at 185 nm, or between 200 and 280 nm with most of the emission at wavelength of 254 nm. The UV light could be generated by light emitting diodes (LEDs) that emit light at specific wavelengths between 260 and 500 nm. This includes emissions in the spectra referred to as UVA, UVB or UVC. An array of LEDs may be used to generate UV light at various wavelengths to achieve different objectives, such as enhancing the reaction rates of different molecules with ozone, or breaking down specific molecules, or breaking down DNA or proteins in microbes. Ozone may be generated from UV lamps that emit at wavelengths of 170 to 190 nm, and preferably at 185 nm. Ozone may also be generated from corona discharge units. The modular sections may also include a filter that removes particulate matter. The filter section may be preferably positioned so that the ultraviolet light could shine on the side of the filter that traps particles. Another modular section could be a catalyst section that oxidizes a variety of chemicals. This catalyst section could be configured with sheets of catalyst that are separated by spacers.

Another modular section could be a catalyst that is specifically configured to remove ozone from the air. This catalyst sections also could be configured with sheets of catalyst that are separated by spacers. Another modular section could be an adsorbent material that at least temporarily removes VOCs from the air at one rate and releases the VOCs at a second rate that may allow more complete conversion of these VOCs by the catalytic system. Another modular section could be a heater that could increase the temperature of the air to add warmth to the room. Heating the air would reduce the chill that an air purifier can cause by operating at relatively high air flow rates in a cold room. The heater could also heat the air to be treated so that the reaction rates across the catalyst are increased. Another modular section could be a UV light that shines or emits UV light in the catalyst layers, either at the catalyst exit or between the catalyst layers. Another modular section of the air treatment unit could be a heat exchanger to remove the heat from the treated air before returning the air to the room. Another module of the air treatment unit could be a fan to induce flow through the modular sections of the air treatment unit.

The modular units can be oriented such that the louvers allow the air to enter the unit, the ozone generating section is downstream of the inlet air louvers. In some embodiments of this invention, UV light section is downstream of the inlet louvers, the filter is down stream of the UV light sections, the first catalyst section is downstream of the filter, the second catalyst section is down stream of the first catalyst section, and an air mover is positioned near the air outlet configured to draw the air through the air inlet into the air treatment zone from outside the housing, moving the air through the entire or all of the air treatment zone and then emitting the air through the air outlet out of the apparatus. An adsorbent layer can be located between the inlet louvers and the air mover.

In some embodiments, the apparatus for treating air further includes a proximity sensor attached to the housing, wherein the proximity sensor detects the presence of a cover outside the housing.

In some embodiments, in the apparatus for treating air, the proximity sensor is a magnetic proximity sensor.

In some embodiments, in the apparatus for treating air, the UV light source is turned on only if the proximity sensor detects the presence of the cover on the apparatus.

In some embodiments, the apparatus for treating air further includes a power connector that connects to a power source.

In some embodiments, in the apparatus for treating air, an interior surface of the housing in the air treatment zone is made of a metal or at least partially coated with a reflector layer.

In some embodiments, in the apparatus for treating air, the interior surface of the housing in the air treatment zone is made of or at least partially coated with aluminum.

In some embodiments, a catalyst used comprises manganese dioxide.

In some embodiments, a catalyst used is supported on a material such as a metallic honeycomb, a metallic corrugated support, a ceramic corrugated support, a ceramic extruded support, expanded metal and/or porous foam.

In some embodiments the support structures for the catalyst have openings in the range of 100 to 1000 cells per square inch.

In some embodiments the air treatment system includes a controller that can independently operate the multiple ozone generators, the multiple UV light emitters, the heater, and/or the fan speed in order to create various modes of air cleaning that target specific contaminants or provide the self-cleaning function for the device.

In some embodiments, the apparatus for treating air further includes a ballast configured to convert power received from the vehicle to higher frequency and higher voltage suitable for the apparatus.

In some embodiments, in the apparatus for treating air, the ozone generator includes an ultraviolet light source.

In some embodiments, in the apparatus for treating air, the contaminant removal zone includes a catalyst that oxidizes contaminants or partially oxidizes contaminants.

In some embodiments, in the apparatus for treating air, the ozone remover includes catalyst that decomposes ozone.

In some embodiments, in the apparatus for treating air, the ozone generator comprises an ultraviolet (UV) light source, and the UV light from the UV light source treats the air in the air treatment zone and the particulate filter.

In some embodiments, in the apparatus for treating air, the ozone generator comprises a corona discharge unit.

In some embodiments, in the apparatus for treating air, the particulate filter comprises a High Efficiency Particulate Arresting (HEPA) filter.

In some embodiments in the apparatus for treating air, the aerosol filter comprises a metal mesh and/or a metal screen filter.

In some embodiments in the apparatus for treating air, the particulate filter comprises materials that can tolerate exposure to UV light and ozone, such as a filter made of glass fibers, or a filter coated with a resistant material such as a fluorocarbon, such as a Teflon® material.

In some embodiments, the particulate filter comprises a layered material where one layer can serve to protect the second layer from UV light. These layers can be combined of glass fibers, carbon fibers, and/or fibers of other spun plastic that are compatible with ozone and UV light.

In some embodiments, in the apparatus for treating air, the UV light source comprises a first UV lamp generating UV light in the wavelength of about 185 nm.

In some embodiments, in the apparatus for treating air, the UV light source further comprises a second UV lamp generating UV light in the wavelength of about 200-300 nm.

In some embodiments, in the apparatus for treating the air the UV light source further comprises a UV source generating UV light at a wavelength in a spectrum between 200 and 500 nanometers in wavelength.

In some embodiments in the apparatus for treating the air the UV light sources is an LED operating at a specific wavelength between 200 and 500 nanometers in wavelength.

In some embodiments, in the apparatus for treating the air the UV light source is an array of LEDs operating at a number of wavelengths between 200 and 500 nm.

In some embodiments, the apparatus for treating air further includes a second UV lamp generating UV light positioned downstream of the inlet and/or the catalyst layers.

In some embodiments, in the apparatus for treating air, the particulate filter allows the ozone generated by the ozone generator to penetrate the particulate filter to treat both upstream and downstream sides of the particulate filter.

In some embodiments, in the apparatus for treating air, the particulate filter allows the ozone generated by the ozone generator to penetrate the particulate filter to treat an inlet of the ozone removal zone.

In some embodiments, the apparatus for treating air further comprises a pre-filter positioned upstream of the particulate filter and downstream of the air treatment zone.

In some embodiments, in the apparatus for treating air, the pre-filter comprises a loose weave filter.

In some embodiments, in the apparatus for treating air, the pre-filter is positioned upstream of the air treatment zone.

In some embodiments, the apparatus for treating air further includes a pre-filter positioned upstream of the particulate filter and downstream of the air treatment zone, wherein the pre-filter allows the UV light from the UV light source to penetrate the pre-filter to treat the particulate filter.

In some embodiments, in the apparatus for treating air, the air mover comprises a volute and a fan, with the volute being connected to an upstream of the fan.

In some embodiments, the apparatus for treating air further includes a material that can adsorb gases, at least temporarily. While adsorbing materials such as activated carbon and/or potassium permanganate, may not permanently hold the contaminants, they may adsorb and then desorb the gases at different rates, allowing the adsorber to change the rate at which the contaminants are released into the rest or remainder of the air treatment system. A layer of adsorbing material, such as activated carbon could be located upstream of the prefilter, downstream of the prefilter, upstream of the aerosol filter or downstream of the air filter, upstream of the catalyst bed or downstream of the first layer of catalyst in the catalyst bed.

In some embodiments, the apparatus for treating air further includes a user interface module configured to receive user input and present information to the user, and an electronic control module configured to set the apparatus to operate in one of a plurality of operation modes, wherein the plurality of operation modes include a regular operation mode, where the ozone generator is on and the air mover operates at a first speed.

In some embodiments, in the apparatus for treating air, the electronic control module is configured to set the apparatus to operate in one of a plurality of operation modes automatically based on at least one of output of at least one sensor and time.

In some embodiments, in the apparatus for treating air, the electronic control module is configured to set the apparatus to operate in one of a plurality of operation modes automatically based on at least one of an output of at least one other appliance and time. In some embodiments, in the apparatus for treating air, the at least one sensors is placed near the air inlet, near the air outlet, or both.

In some embodiments, in the apparatus for treating air, the at least one sensor detects occupancy of an ambient environment where the apparatus is positioned or situated.

In some embodiments, in the apparatus for treating air, the at least one sensor detects a contaminant content and level of an ambient environment where the apparatus is positioned or situated.

In some embodiments, in the apparatus for treating air, the electronic control module is configured to set the apparatus to operate in one of a plurality of operation modes based on the user input.

In some embodiments, in the apparatus for treating air, the plurality of operation modes further include a self-cleaning mode, where the ozone generator is on, the ozone generated by the ozone generator treats and cleans interior components of the apparatus, and the air mover operates in a second speed lower than the first speed.

In some embodiments, in the apparatus for treating air, the plurality of operation modes further include a self-cleaning mode, where the ozone generator is on, the ozone generated by the ozone generator treats and cleans interior components of the apparatus, and the air mover operates in a second speed lower than the first speed, with the second speed set to reduce the space velocity through the catalyst to less than 100,000 hr-1.

In some embodiments, the apparatus for treating air further includes a user interface module configured to receive user input and present information to the user, and an electronic control module configured to set the apparatus to operate in one of a plurality of operation modes, wherein the plurality of operation modes include a regular operation mode, where the ozone generator is on and the air mover operates at a first speed.

In some embodiments, in the apparatus for treating air, the plurality of operation modes further include a self-cleaning mode, where the UV light source is on, the UV light from the UV light source and the ozone generated by the UV light source treat and clean interior components of the apparatus, and the air mover operates in a second speed lower than the first speed.

In some embodiments, in the apparatus for treating air, the UV light source comprises a first UV lamp generating UV light in the wavelength of about 185 nm and a second UV lamp generating UV light in the wavelength of about 254 nm, and the plurality of operation modes further include an ozone removal mode, where the first UV lamp is off and the second UV lamp is on.

In some embodiments, in the apparatus for treating air, the plurality of operation modes further include a particle removal only mode, where the ozone generator is off.

In some embodiments, the apparatus for treating air further includes a wireless communication module configured to communicate with a central management system.

In some embodiments, in the apparatus for treating air, the electronic control module sets the apparatus to operate in one of the plurality of operation modes based on instructions received from the central management system via the wireless communication module.

In some embodiments, in the apparatus for treating air, the instruction is at least partially based on information received from another appliance.

In some embodiments, in the apparatus for treating air, the instruction is at least partially based on information received from the system that the appliance is built into.

In some embodiments, the apparatus for treating air can be built into the kitchen cabinets and connected electronically to the range and the ventilation hood. The electronic control of the apparatus could be configured to operate a set operating cycle that includes a schedule of operating modes including cleaning air from the room, self-cleaning, and deodorizing the unit itself. The duration and elements of the cycle could be customized by the home owner by providing the controller information about the size of the kitchen, for example. The timing of the cycle could be defined by the timing of the operation of the range, or other cooking appliance that could create food odors in the kitchen, and the operation of the ventilation hood, which generally operates when the range or cooktop is in operation. The air treatment apparatus could be configured to operate after the range has been used and the ventilation hood has been turned off. Residual odors in the room would then be removed in a set cleaning cycle. An example of an operating cycle is as follows: the air treatment system operates at high flow, for example 100 to 200 cfm with no ozone bulb operating in order to rapidly collect aerosols of grease or smoke from the room. Subsequent to this aerosol cleaning period, the air flow could reduce to 50 to 150 cfm with both the ozone generating bulb and a germicidal bulb operating upstream of the grease filter. In this mode a UV bulb operating downstream of the initial catalyst layer can also be operating. After a cleaning cycle of approximately 1-3 hours, corresponding to 1 to 15 air exchanges of the room, the air treatment system could reduce its flow rate to 10 to 30 cfm in order to deodorize and oxidize the material collected on the grease filter and catalyst. During this self-clean cycle either UV only or ozone bulbs downstream of the first catalyst layer could be operated independently or together. This self-clean cycle could be maintained for 0.5-3 hours. These cycle elements could be operated in any sequence depending on the nature of the air in the kitchen.

In some embodiments, the apparatus for treating the air can be built into or installed in an automobile. VOCs can be emitted by the interior plastics and fabrics in a new car. This emission rate can be significantly increased when the car interior is heated, such as by the sun. Such VOC emissions can be controlled using a built in air treatment system that converts rather than captures these VOCs.

Such an air cleaner can be built into the automobile and can be equipped with a variable speed fan to allow for the adjustment of air flow and hence the treatment rate of the air in the car cabin. In addition, UV and/or ozone generating devices can be switched on or off.

In one embodiment, control of the air cleaner can be initiated via a mobile phone application. For example, if the car interior temperature exceeds a certain value, the air cleaner can be automatically operated. Furthermore, operating modes can be selected depending on the presence or absence of vehicle occupants. For example, high airflow provides higher treatment rates, but can be too noisy for certain vehicle occupants.

In one embodiment, a driver anticipates using the car at a certain time and via an app, starts the air cleaner some time (e.g., 5-30 minutes) before entering the car. The air cleaner can remove the VOCs from the interior and then shut off when the driver enters the vehicle. In another use case, a person smokes cigarettes during a drive. The user than activates the air cleaner on exiting the vehicle and the air cleaner runs for a specified cycle to remove the odor of cigarettes from the interior of the car.

In some embodiments the apparatus for cleaning air can be built into a reach-in refrigerator. The electronic control of the apparatus could be configured to operate in response to various outputs from the refrigerator such as the door switch, the evaporator fan operation, and the compressor operation. In one embodiment, the air cleaning apparatus turns off when the door is opened. In another embodiment, the air cleaning apparatus turns on for a set interval after the door has been closed or shut. In one embodiment the air cleaning apparatus turns on only if the evaporator fan is operating. In another embodiment the air cleaning apparatus turns on or off if the compressor has not been operating for a set period of time.

The details of one or more variations of the subject matter described herein are set forth in the accompanying drawings and the description below. Other features and advantages of the subject matter described herein will be apparent from the description and drawings, and from the claims.

DESCRIPTION OF DRAWINGS

FIG. 11A shows a table that lists different configurations of an air purifier that can be achieved by including or excluding the modular components illustrated in FIG. 1.

FIG. 11B shows a table that lists additional configurations of an air purifier that can be achieved by including or excluding the modular components illustrated in FIG. 1.

Throughout this specification and in the claims, like reference symbols in the various drawings indicate like elements.

DETAILED DESCRIPTION OF THE INVENTION

Throughout this specification and in the claims, the terms air cleaning unit and atmosphere treating unit are intended to relate to an apparatus for sanitizing, filtering, decontaminating, deodorizing, purifying, conditioning, heating, humidifying, drying and/or otherwise treating, cleaning, modifying and/or improving an atmosphere within a space.

Figure 1:
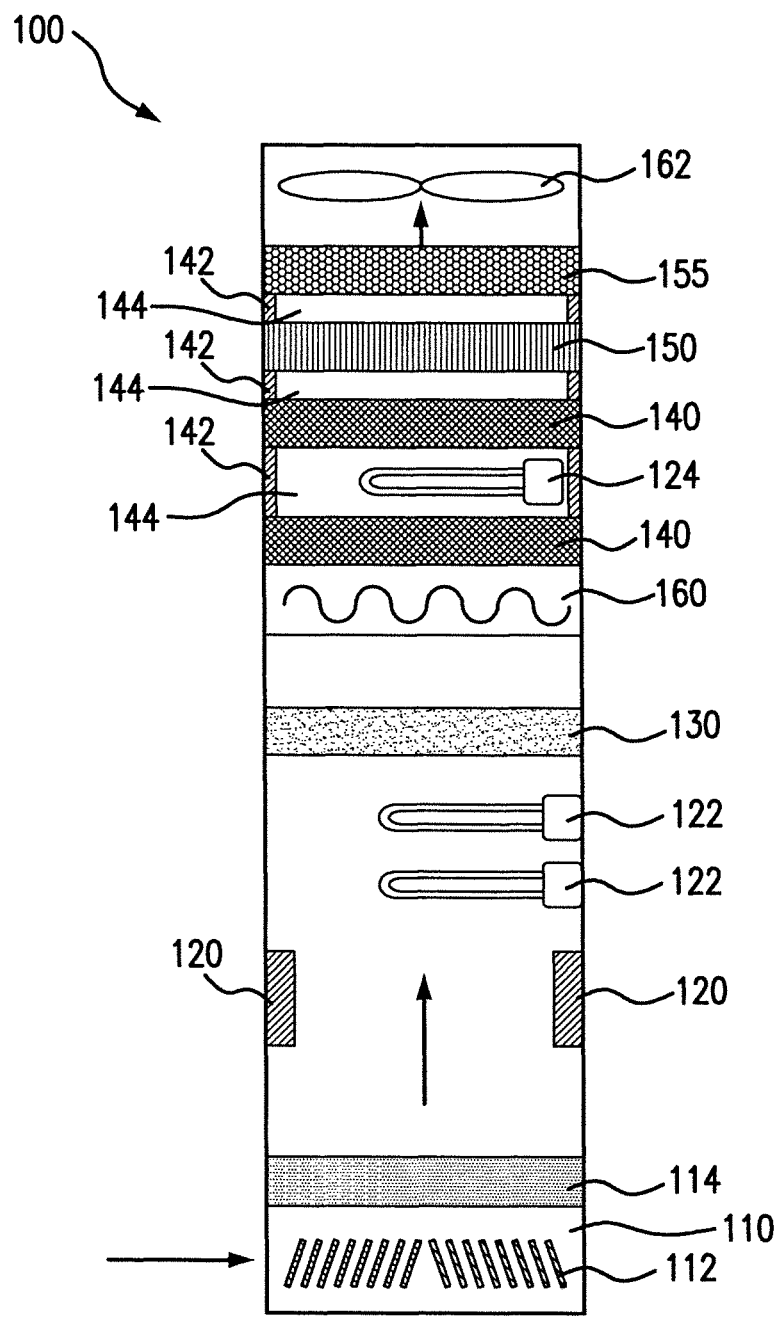
FIG. 1 shows a schematic view of an apparatus for treating air, according to one embodiment of this invention.

FIG. 1 is a schematic view of a modular air treatment system 100 of components that can be combined in various ways to achieve some objectives of the air treatment system of this invention. The schematic shows an air inlet section 110 to receive an air flow illustrated by arrows. The air inlet section 112 has baffles 112 to contain light generated inside the air treatment system. The schematic also shows a prefilter 114 that can remove large material from entering the treatment areas of the air treatment system 100. Downstream of the prefilter 114 is one or more of an ozone generator 120 and/or a UV light source 122. The ozone generator 120 may be a UV bulb emitting at frequencies less than 200 nm, or it may be a corona discharge unit. The UV light source may be a mercury lamp emitting at wavelengths above 200 nm or it may be one or an array of light emitting diodes that emit at a wavelength inside the UV spectrum from 200 to 500 nm. Downstream of the UV lights 122 is a particulate filter 130 that is exposed to some combination of ozone and UV light. This filter 130 can be, for example, made of fiberglass to collect particulate matter or can be made of metal mesh to collect aerosols of grease and smoke.

Downstream of the filter 130 are catalyst layers, such as formed of a plurality of catalyst sheets, which may be one or more formulations and structures, depending on the desired performance of the air treatment unit. A first set of catalyst layers 140 may be oxidizing catalysts that break down chemical contaminants, and extend across an air treatment zone. A second catalyst layer 150 may be ozone removal catalysts and extend across an ozone removal zone. In embodiments of this invention, each catalyst layer is spaced apart from an adjacent catalyst layer, such as by spacer elements 142. The resulting air space 144 between adjacent catalyst layers desirably acts to allow or create a more mixed or turbulent air flow through the catalyst layers. This prevents or disrupts a linear air flow through the catalyst material, such as when the catalyst layers have a matching honeycomb passageway configuration. A further catalyst layer 155 is downstream of the second catalyst layer 150. The further catalyst layer 155 can include the first catalyst material, the second catalyst material, or a third catalyst material. In FIG. 1, the further catalyst layer 155 includes the second catalyst material.

A heater 160 may be positioned upstream of the catalysts 140. A fan 162 is positioned downstream of the catalyst layers 140 and 150.

In FIG. 1, additional UV bulb 124, either ozone generating or not ozone generating, is positioned between the catalyst layers 140. The additional UV bulb 124 is downstream of one of the first catalyst layer 140, and can be alternatively be disposed between the first catalyst layers 140 and the second catalyst layer 150, or between the second catalyst layer 140 and the further layer 155, depending on need. In addition, multiple additional UV sources can be placed between the spaced apart catalyst layers, depending on need.

Figure 2:
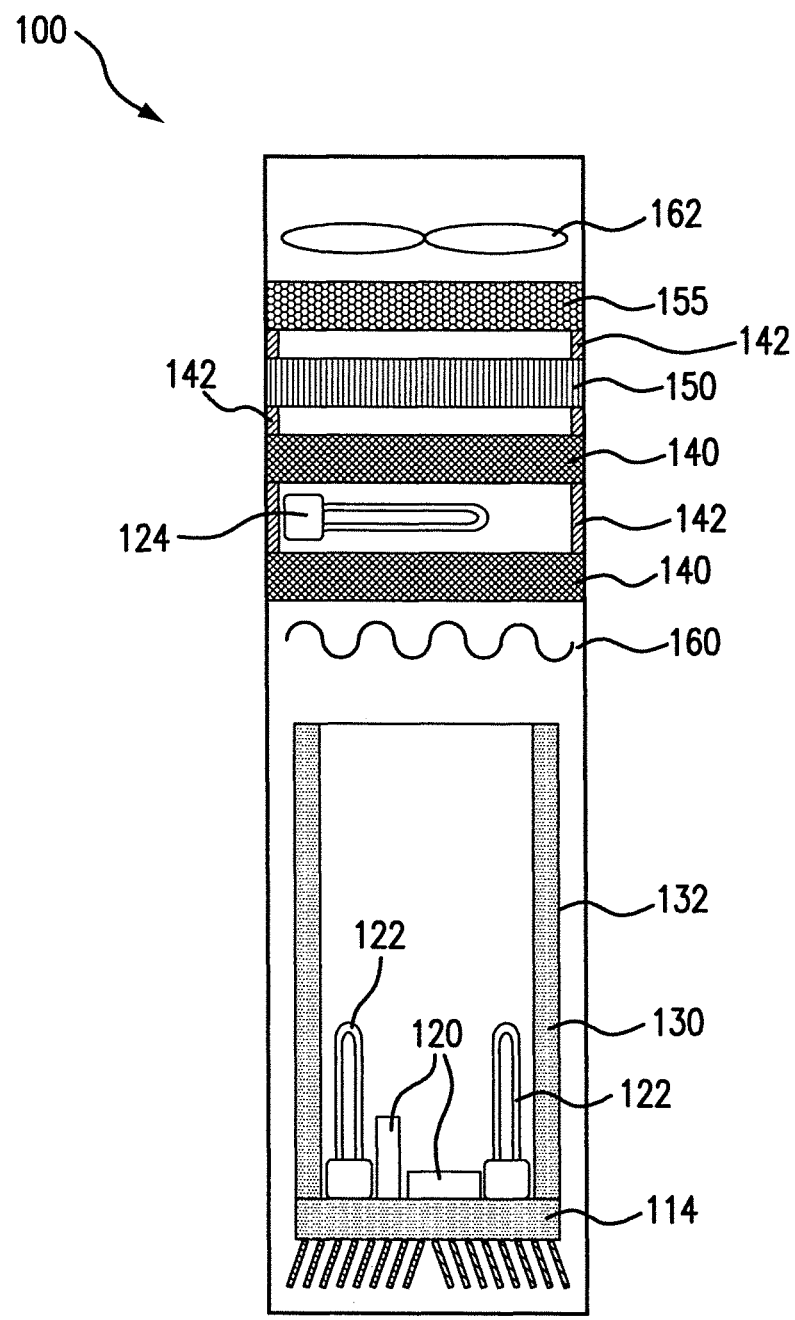
FIG. 2 shows a schematic view of an apparatus for treating air, according to one embodiment of this invention.

FIG. 2 is a schematic of a modular system of components similar to FIG. 1, but illustrating an alternative configuration. In FIG. 2 the particle and/or grease removal filter 130 has a cylindrical geometry. An adsorbent layer 132 has been added to this modular system of air cleaning components. The adsorbent layer is illustrated on an outside surface of the cylindrical filter 130 (desirably away from UV source 122), and can additionally or alternatively be on an inlet side of the prefilter 114 and/or the inlet side of the most upstream first catalyst layer 140.

Figure 3:
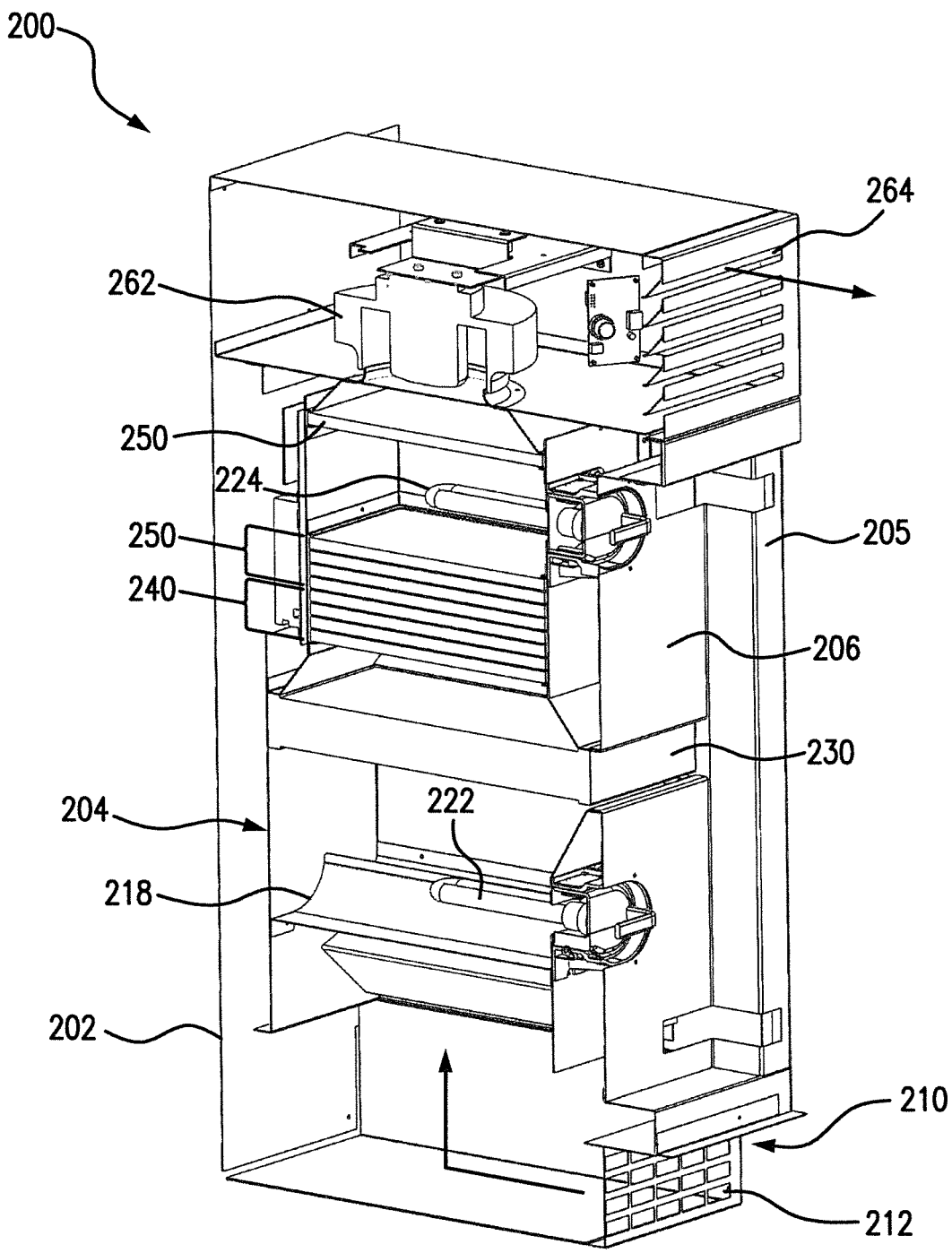
FIG. 3 shows a perspective, sectional view of an apparatus for treating air, according to one embodiment of this invention.
Figure 6:
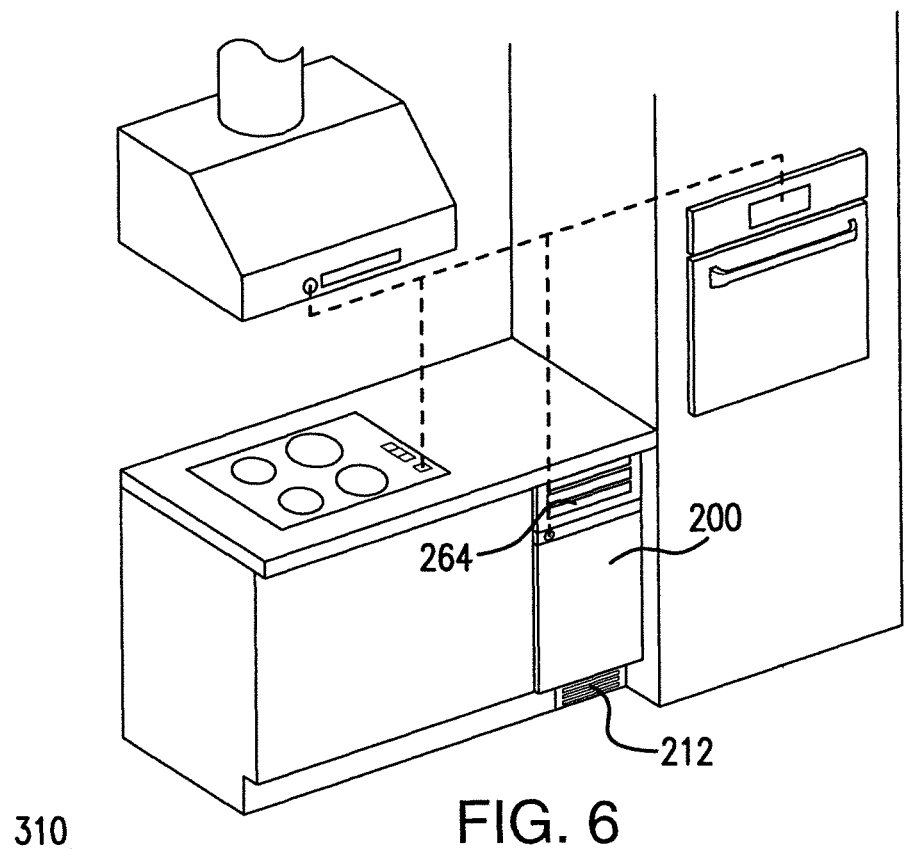
FIG. 6 shows a schematic view of an air treatment system built into the cabinetry of a kitchen.

FIG. 3 is an illustration of an air treatment apparatus 200 configured to be built into kitchen cabinetry (See FIG. 6). The apparatus 200 includes a housing 202 enclosing a module construction, with functional components formed as modular attachments that are attachable to the housing 202. For example, a first attachable module 204 includes an ozone generator, a second attachable module 206 includes the first and/or second catalyst layers, and at least one further attachable module includes an air inlet baffle 210, a particle material filter 230, or an air mover assembly 262. The modules can be attached by any suitable means, such as by fastening on a module attachment element 205 of the housing 202.

In FIG. 3, the air inlet baffle 212 and air outlet 264 are locked on the same lateral side of the apparatus 200, allowing the air to be drawn into the air treatment apparatus from the room and exhausted back into the room (See FIG. 6). The three other vertical sides of the air treatment apparatus 200 can be between cabinets or a wall. The air enters the apparatus from the bottom of the unit, turns about 90 degrees and flows around a curved baffle 218 designed to contain the UV light 222 in the apparatus 200 without adding significant pressure drop to the system. The UV lamps 222, including one or both that generate ozone, are positioned upstream of the grease filter 230. After passing through the grease filter 230, where aerosols of grease and smoke are removed from the air, the air passes through a plurality of spaced apart low temperature oxidizing catalyst layers 240. The air subsequently passes through spaced apart ozone reduction catalyst layers 250. Between or within the plurality of ozone reduction catalyst sheets/layers 250 is another set of UV bulbs 224 that may or may not generate additional ozone. The UV light and/or ozone can be used to for further oxidation and/or to clean the catalyst layers 250.

In embodiments of this invention, the ozone and UV light together create active species that support continued oxidation of chemical bound to the active sites in the catalysts. These active species also serve to help the oxidized chemicals desorb from the catalyst. There may be multiple layers of both catalyst types in the apparatus. The air flow is drawn through a fan 262 and exits through a set of baffles 264 designed to allow free flow of clean air while preventing any backflow or penetration back into the fan area. The outlet grill 264 distributes the air flow so that it exhausts slowly and evenly and does not blow noticeably on a person standing close to the apparatus.

Figure 4:
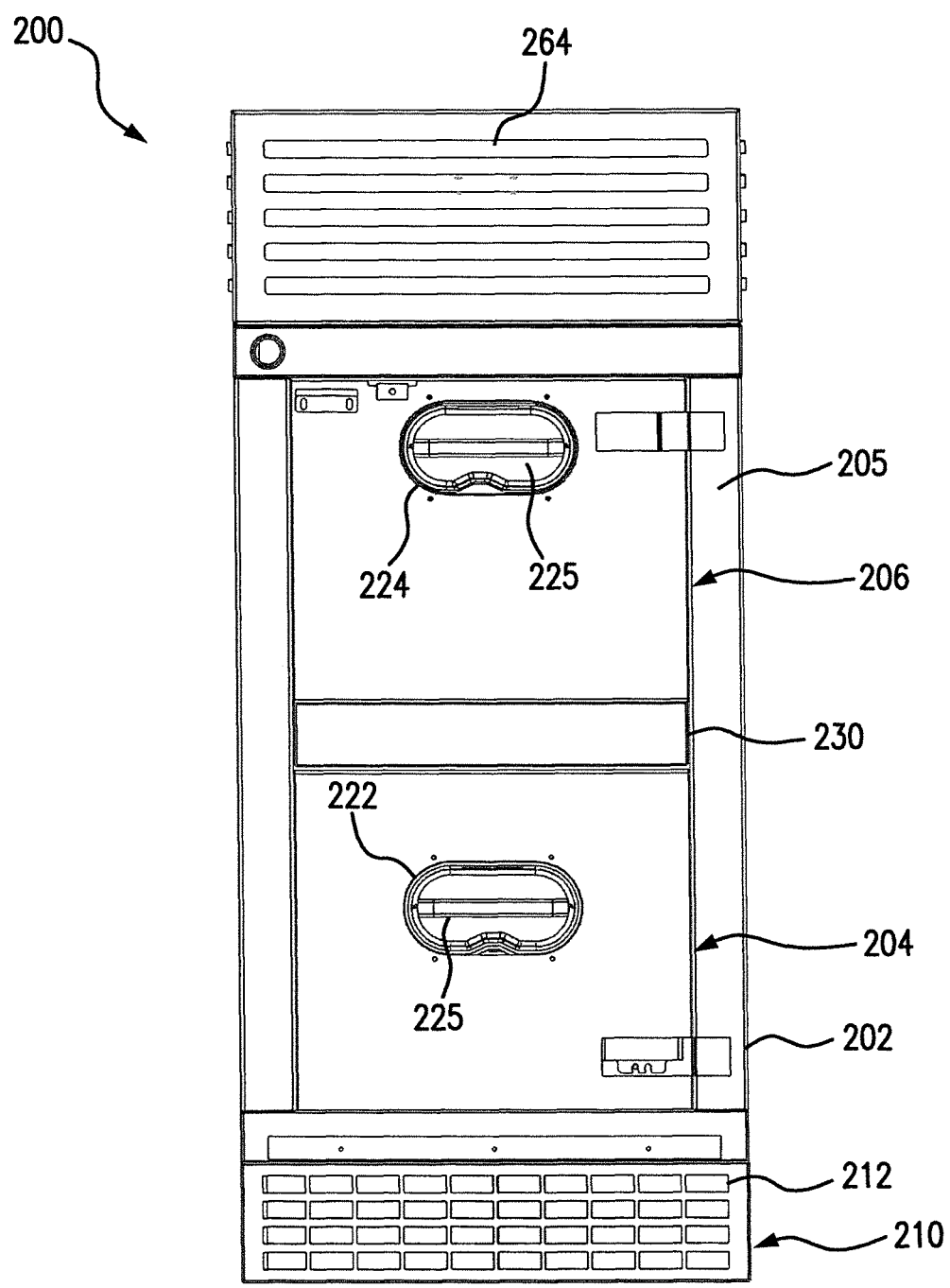
FIG. 4 shows a front view of an apparatus for treating air, according to one embodiment of this invention

FIG. 4 shows a front view of the apparatus 200. The dual bulb cartridges 222 and 224 are configured to be easily removable by pulling firmly on the cassette handle 225. The bulb connects to a socket with multiple connector points (See FIG. 12A), allowing the apparatus to sense whether the bulb is properly positioned or in place.

Figure 5:
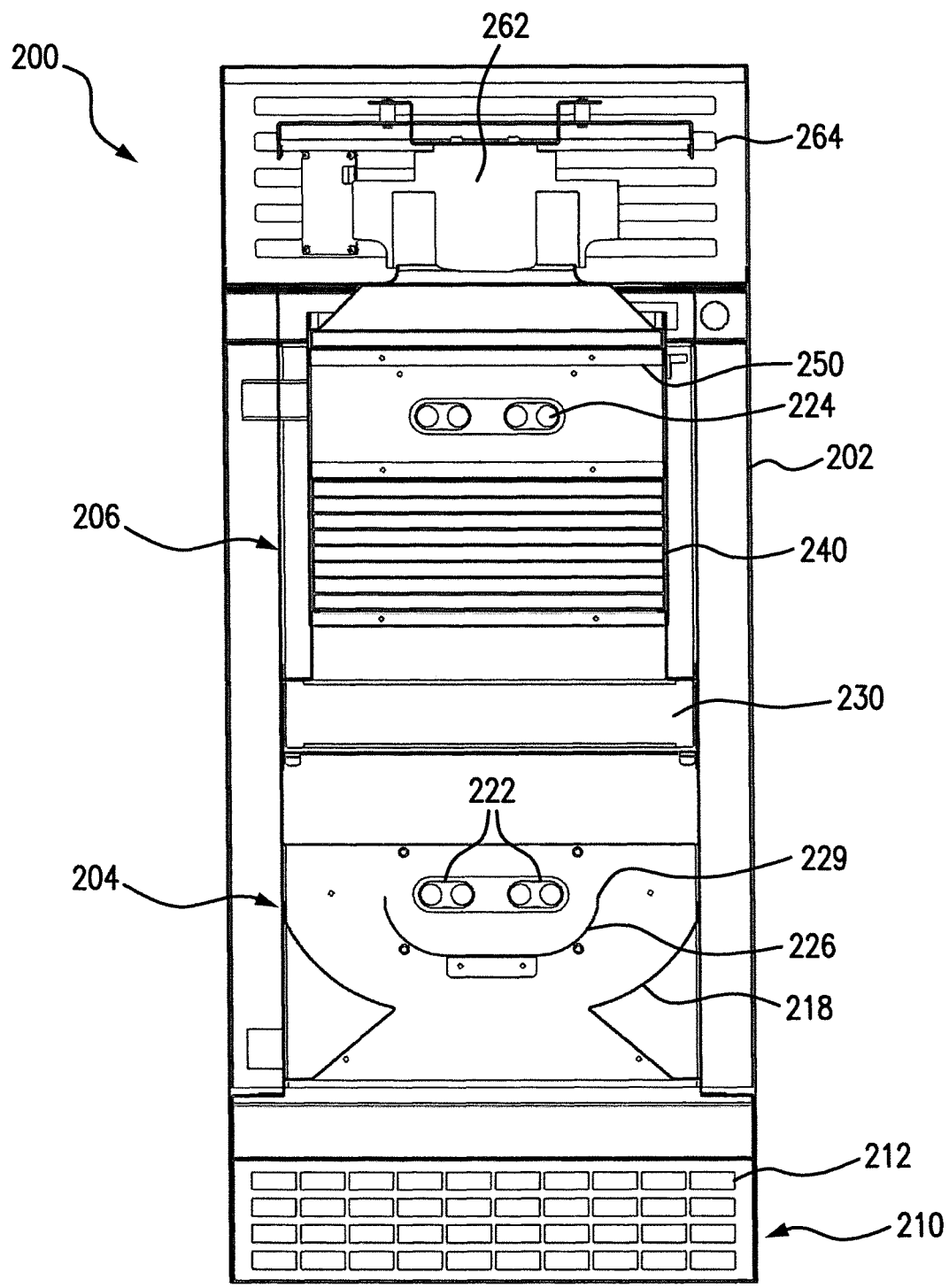
FIG. 5 shows a cross section of a front view of an apparatus for treating air, according to one embodiment of this invention.

FIG. 5 shows a cross section of the apparatus 200 and illustrates the shape of the concave UV baffle 218 and bulb reflector 226. The matching curved surfaces of the bulb reflector 226 and the air inlet baffle 218 contain the UV light and prevent the light from exiting the bottom of the apparatus without creating significant pressure drop for the air to flow into the body of the apparatus. The second set of UV lamps is located between the catalyst layers, downstream of the first layers 240 and upstream of the fan 262. The curved surface of the bulb reflector 228 has an increase in the curvature at each edge 229 of the reflector to ensure containment of the UV light.

FIG. 6 shows the built-in air treatment system 200 installed in cabinetry in a kitchen in electronic communication with a cooking appliance and a ventilation hood. The built-in air treatment system could be installed under the counter at any location in the kitchen. The apparatus is controlled by outputs from the surrounding environment, selected from environment sensors and/or operation of fans, motors, or appliances, separate and independent from the apparatus. Referring to FIG. 6, the air treatment system 200 has a control device (with necessary hardware, data processors, and encoded software instructions) that can communicate with a range, a cooktop and/or the ventilation hood via wired or wireless connections. The wireless communication could be a local area network, Bluetooth connection, Wi-Fi, infrared or other means of allowing the air treatment system 200 to operate based on the modes or states of the cooking appliance and ventilation hood.

Figure 7:
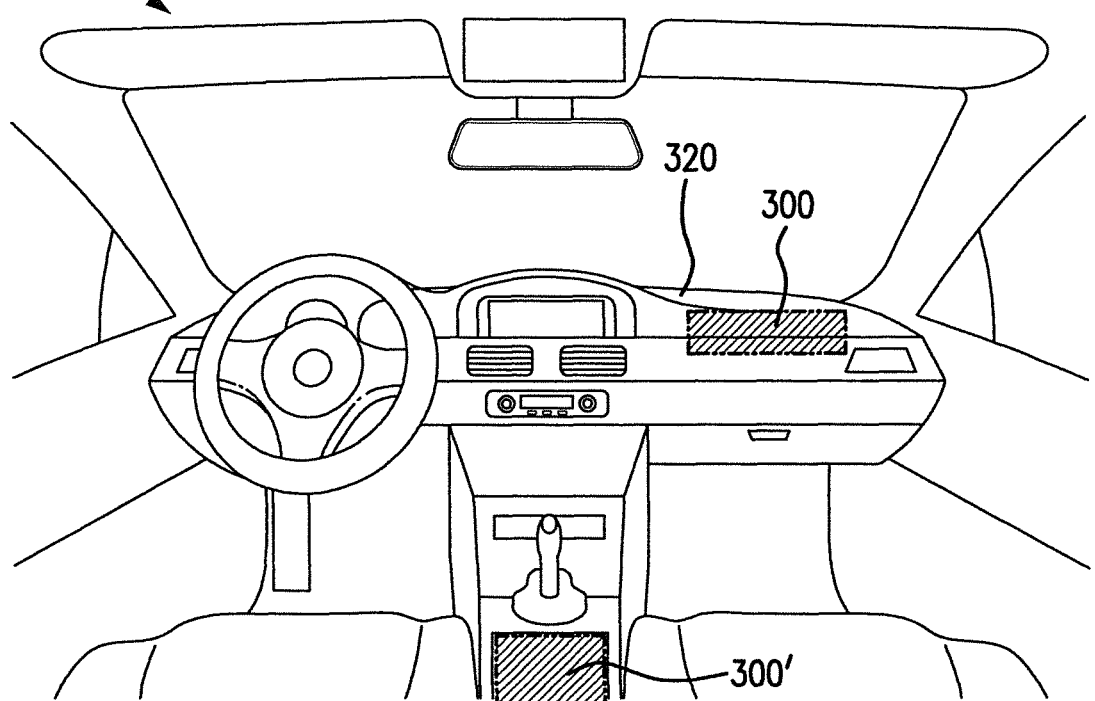
FIG. 7 shows a schematic view of an air treatment system built into the cabin of an automobile.

FIG. 7 shows an air cleaning apparatus 300 built into an automobile cabin, located or positioned either in the dashboard (300) or the center console (300') according to some embodiments of the subject matter disclosed herein. The apparatus for treating air 300 can be mounted on a dashboard inside the automobile. The power connector of the apparatus 200 can be connected to a power source inside the automobile, such as an automobile battery. In some embodiments, the apparatus for treating air 300 can also contain a ballast, which can regulate voltage, current, and/or frequency of the power. The power connector can be connected to the ballast, which can be connected to a power source inside the automobile. In some embodiments, the ballast can be part of the automobile itself. The apparatus 300 can be covered by a decorative and/or protective cover 320.

In some embodiments, the apparatus for treating air 300 can be mounted inside the automobile HVAC system next or close to the air conditioning evaporator. In operation, the air is drawn from the cabin of the automobile 310 into the apparatus for treating air 300. After treatment, the air is emitted from the apparatus 300 into the car cabin or into the HVAC system of the automobile. The air can flow back into the cabin of the automobile through the existing HVAC ducting of the automobile. In some embodiments, the apparatus 300 itself can include no active air mover component. Instead, the apparatus 300, when mounted near or next to HVAC system of the car, can leverage the fan of the ventilation system to function as an air mover. Alternatively, the apparatus 300 can be self-contained with its own fan that draws air from the cabin 310 into the apparatus 300 and back into the cabin 310. In some embodiments a second air mover could be used to mix the exhaust air from apparatus 300 into the cabin 310 and mix the cabin air.

Figure 8:
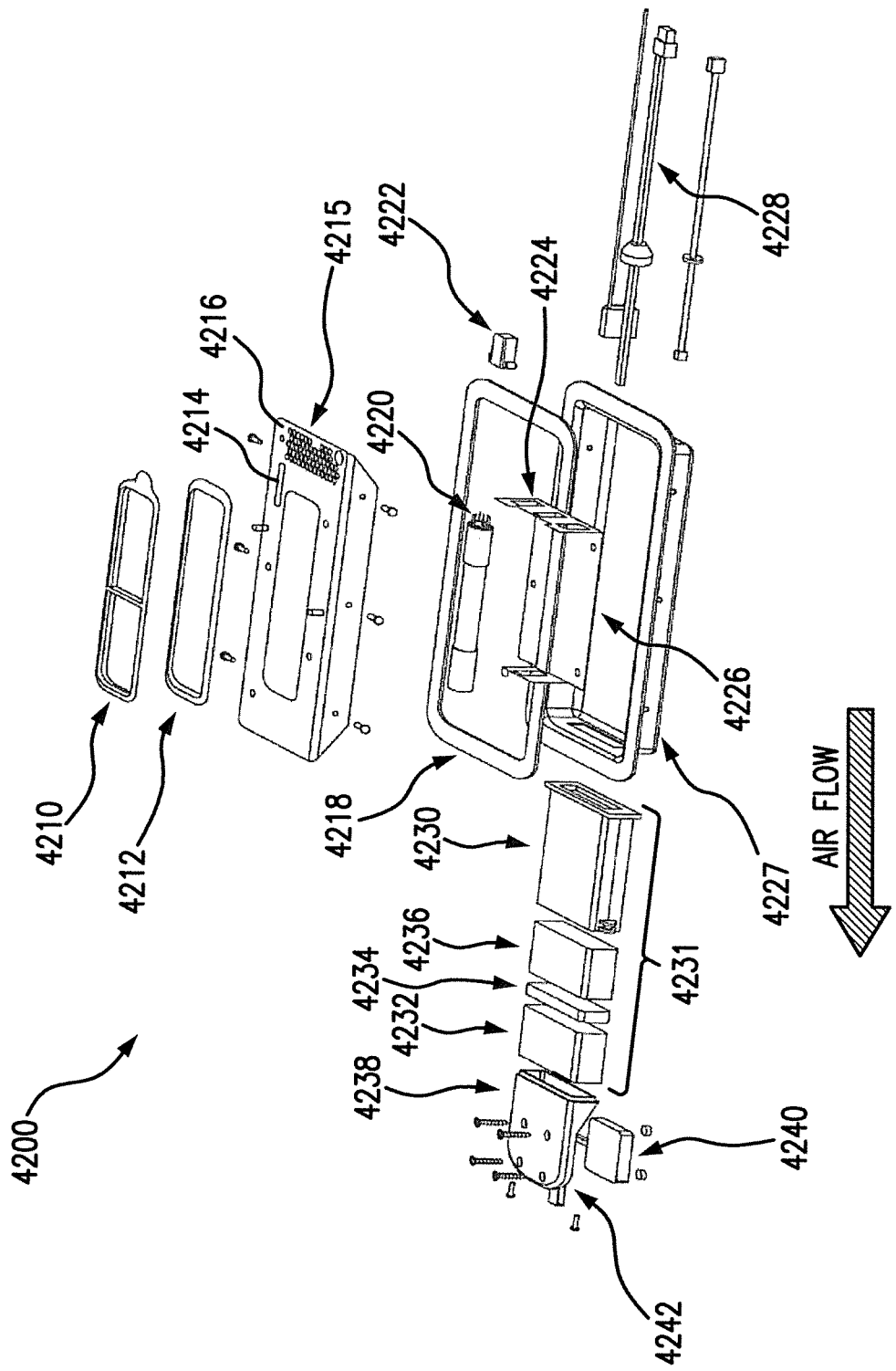
FIG. 8 shows an exploded perspective view of an air treatment system for a refrigerator.

FIG. 8 illustrates an exploded view of an apparatus for treating air 4200 according to some embodiments of the subject matter disclosed herein. The apparatus for treating air 4200 can include a light cover 4210, a cover gasket 4212, a proximity sensor (e.g., magnetic proximity sensor) 4214, an unit cover 4215, an air inlet 4216, a gasket enclosure to evaporator cover 4218, a UV light bulb 4220, a UV light bulb socket 4222, a UV light bulb holding bracket 4224, an air treatment zone 4226, an enclosure of the air treatment zone 4227, power and sensor wires 4228, an ozone removal zone 4231, a catalyst housing 4230, a first catalyst section 4236, a catalyst spacer 4234, a second catalyst section 4232, an air mover (e.g., a fan) 4240, a housing for the air mover 4238, and an air outlet 4242.

The apparatus for treating air 4200 can include a housing with an air inlet (e.g., 4216) and an air outlet (e.g., 4242). In some embodiments, the enclosure for the air treatment zone 4227, the catalyst housing 4230, and the housing for the air mover 4238 can form a multi-section or unibody housing for the apparatus for treating air 4200. The apparatus for treating air 4200 can include an air treatment zone (e.g., 4226) and an ozone removal zone (e.g., 4231). As illustrated in FIG. 8, the ozone removal zone 4231 is positioned downstream of the air treatment zone 4226 with respect to a flow direction of the air being treated.

The apparatus for treating air 4200 can include an UV light source (e.g., 4220) in the air treatment zone 4226 configured to generate ozone from the air. The UV light from the UV light source and the ozone generated by the UV light source can treat (e.g., clean, sanitize, or deodorize) the air in the air treatment zone 4226.

The apparatus for treating air 4200 can include catalyst in the ozone removal zone 4231 that removes at least a portion of the ozone generated by the UV light source (e.g., 4220). As illustrated in FIG. 8, the ozone removal zone 4231 can include the first catalyst section 4236 and the second catalyst section 423, separated by the spacer 4234. The configuration of two separate catalyst sections with a spacer in between can improve the flow of air through the ozone removal zone 4231. For example, the spacer 4234 can allow the air coming out of the first catalyst section 4236 to redistribute before entering into the second catalyst section 4232. The redistribution of air flow can improve the performance of the ozone removal zone 4231. The first catalyst section 4236 and the second catalyst section 4232 could contain the same or different catalyst compositions.

The apparatus for treating air 4200 can include an air mover (e.g., 4230) positioned near the air outlet (e.g., 4242) that can draw the air through the air inlet (e.g., 4216) into the air treatment zone (e.g., 4226) from outside the housing, moving the air through the air treatment zone (e.g., 4226) and the ozone removal zone (e.g., 4231), and then emitting the air through the air outlet (e.g., 4242) out of the apparatus 4200.

The apparatus for treating air 4200 can include a proximity sensor (e.g., 4214). The proximity sensor can be attached to the housing. The proximity sensor can detect the presence of a cover outside the housing of the apparatus 4200. The cover can be protective (e.g., to provide additional shield of the UV light) or decorative. The apparatus 4200 can turn off the UV light source if a cover is not detected. In some examples, the proximity sensor can be magnetic.

The apparatus for treating air 4200 can include a power connector (e.g., 4228). The power connector can be connected to a power source inside a container (e.g., a refrigerator) to provide power to the apparatus 4200. In some embodiments, the apparatus for treating air 4200 can also include one or more sensors to detect the condition of the ambient environment (e.g., temperature, air quality, contaminant content and/or level, etc.).

In some embodiments, the interior surface of the housing of the apparatus 4200 (e.g., in the air treatment zone 4226) can be at least partially coated with a reflector layer (e.g., metal layer such as aluminum). The components of the apparatus can be made in various materials, such as metal or plastics. Certain structural materials (e.g., plastics) can reduce the weight and/or cost of the apparatus 4200, but can deteriorate over time, especially in the presence of UV light. Coating the interior surface of the housing with a reflector layer can shield the structural materials from UV light and extend its usage life; it can also reduce the absorption of UV by the interior surface of the apparatus and enhance the UV light intensity inside the air treatment zone, thus improving the performance of the air treatment zone.

Figure 9:
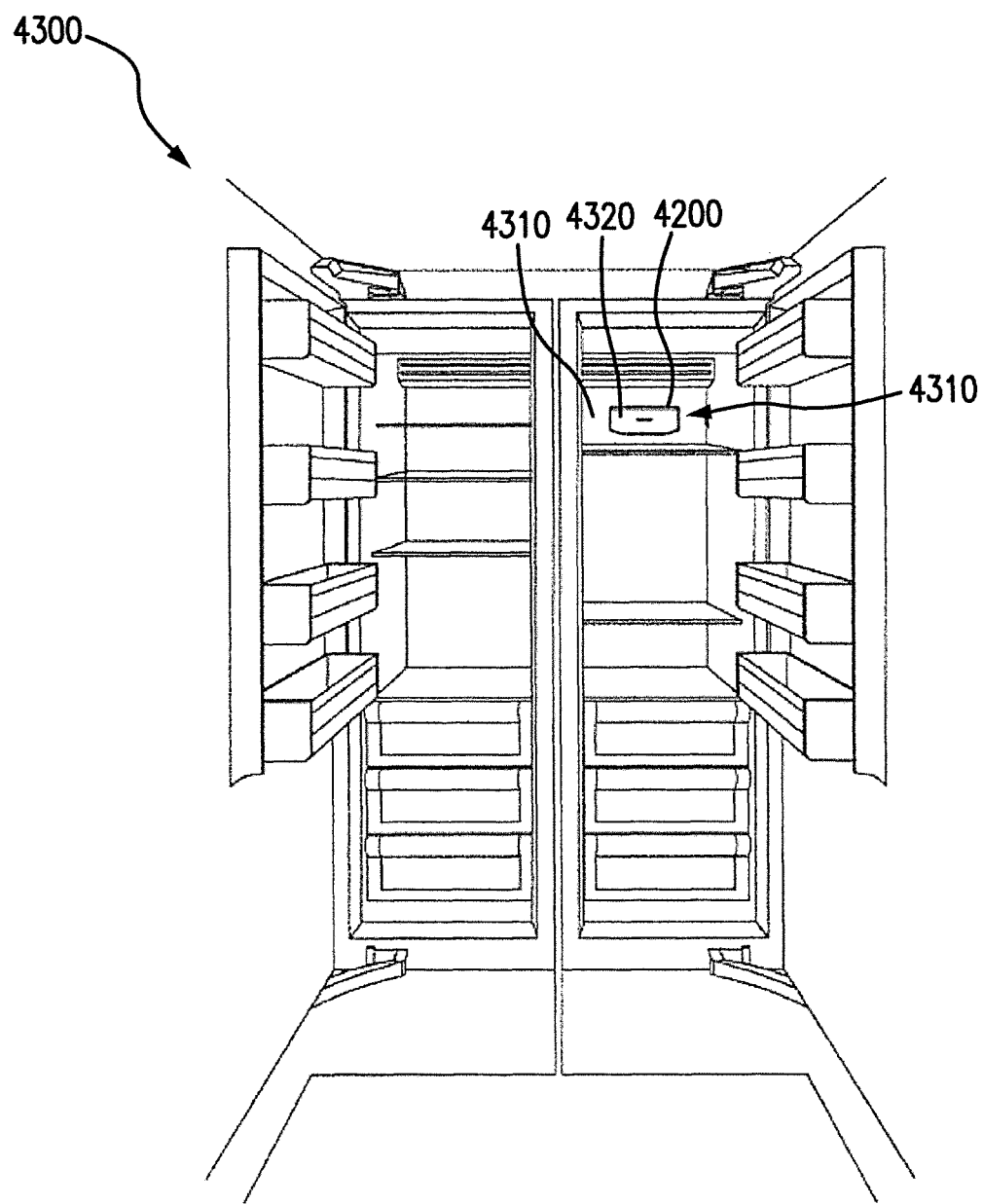
FIG. 9 shows an air treatment system built into a refrigerator.

FIG. 9 shows an air cleaning apparatus 4200 located in the back panel 4310 of a reach-in type refrigerator 4300. The air cleaning apparatus has a decorative front plate 4320 that is configured to protect and allow air flow into the apparatus. The operation of air cleaning apparatus 4200 can be defined by the position of the door switch, the operation of the evaporator fan, and/or the operation of the compressor.

Figure 10A:
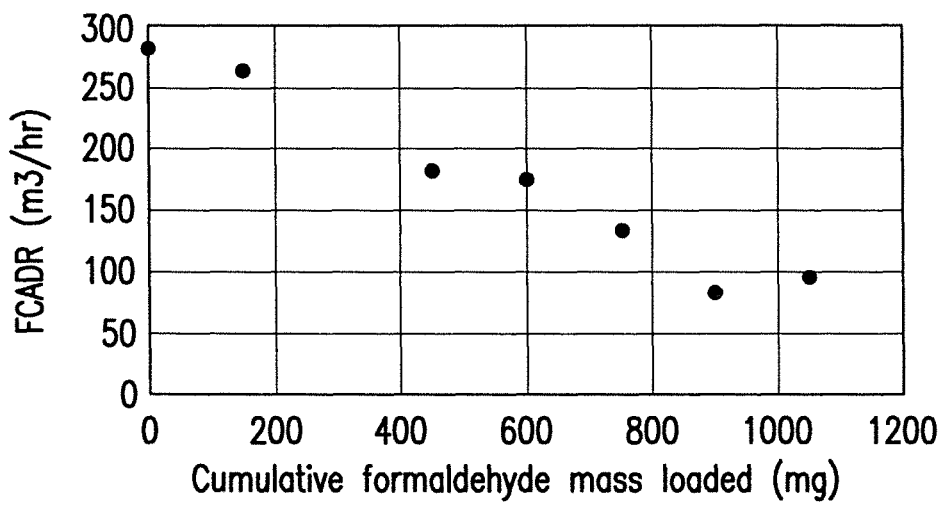
FIG. 10A shows a graph of a control comparison for FIG. 10B.
Figure 10B:
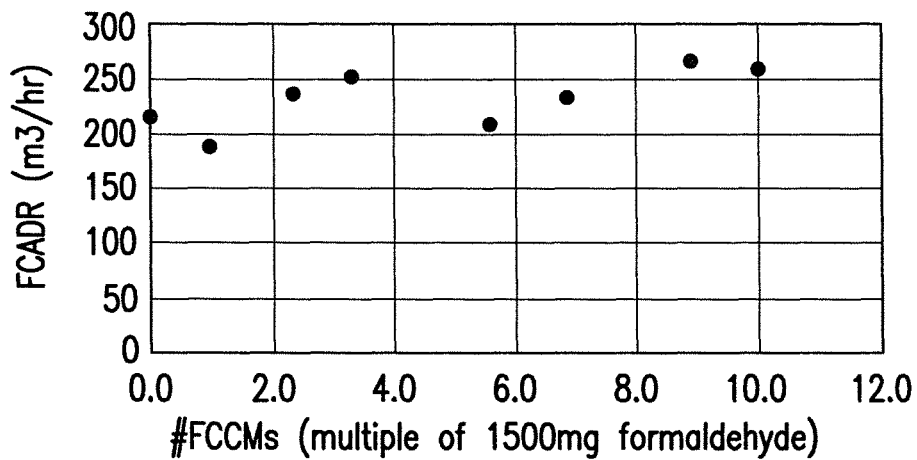
FIG. 10B shows a graph detailing the performance benefit of using ozone to clean a catalyst during a formaldehyde removal cycle.

FIG. 10B is a graph that illustrates the value of ozone in maintaining the formaldehyde removal performance of a low temperature oxidizing catalyst. Without ozone use (FIG. 10A) the performance of the catalyst decays over time. With ozone use, the performance of the catalyst in oxidizing formaldehyde is maintained. This catalyst self-cleaning cycle with ozone provides benefit to the performance of the system.

FIGS. 11A and 11B illustrate the combinations of the modular components described herein that can be combined in different configurations to achieve different performance characteristics of an air cleaning apparatus.

Figures 12A, 12B:
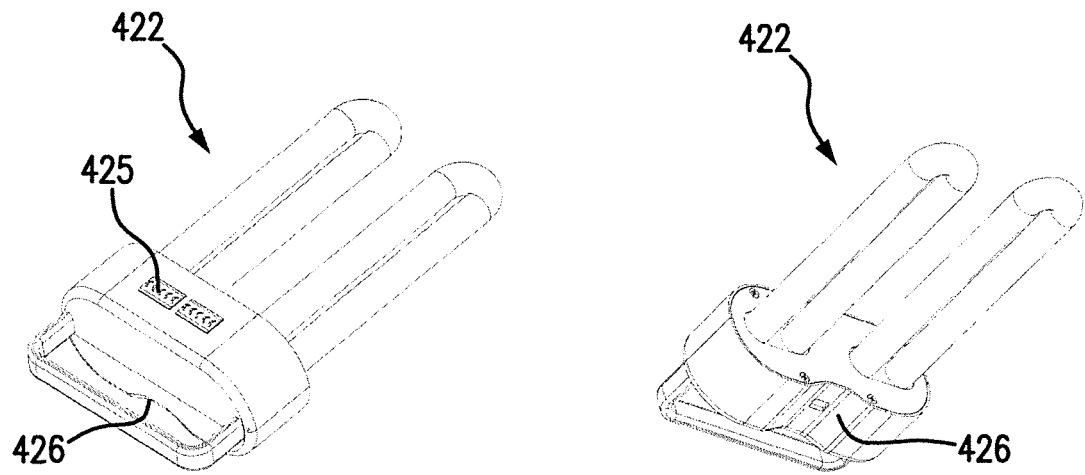
FIGS. 12A and 12B each shows a dual replaceable bulb cartridge that is part of the apparatus for treating air, as shown in FIG. 3.

FIGS. 12A and 12B shows the configuration of a dual bulb replacement cassette 422. The cassette has electrical contacts 425 on one side and a mechanical detent 426 on the underside. The electrical contacts 425 line up with contacts in a corresponding bulb socket. In this configuration, four of the electrical contacts 425 match to contacts in the socket to close and allow power to flow from the ballasts to the bulb and light the bulb. One additional contact is used to close a circuit to the controller to indicate that the bulb has been installed. If the bulb is removed, the check circuit is open and the controller sends an error message to a display indicating that the bulb is not in place.

Figure 13:
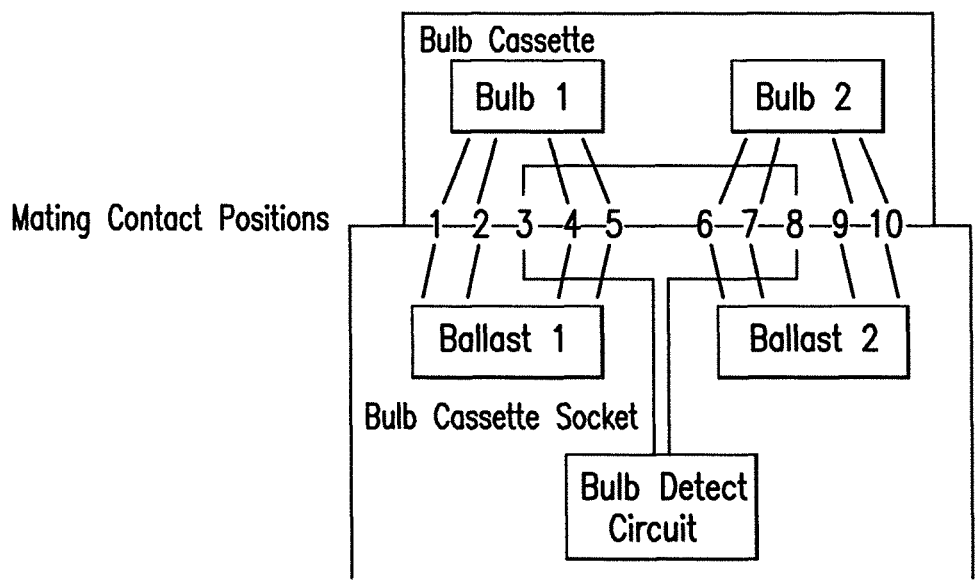
FIG. 13 representatively shows a bulb socket configured to receive the dual replaceable bulb shown in FIG. 12.

FIG. 13 shows an exemplary bulb circuit diagram that illustrates the connections between the bulb cassette and the ballasts that power the bulbs. The contacts that are part of the bulb detect circuit are distinct from the contacts that power the bulbs. In embodiments of this invention, the bulb has an internal circuit between its contacts that closes a circuit to the controller to indicate that the bulb has been installed. If the bulb is removed, the check circuit is open indicating the bulb is not installed.

Figure 14:
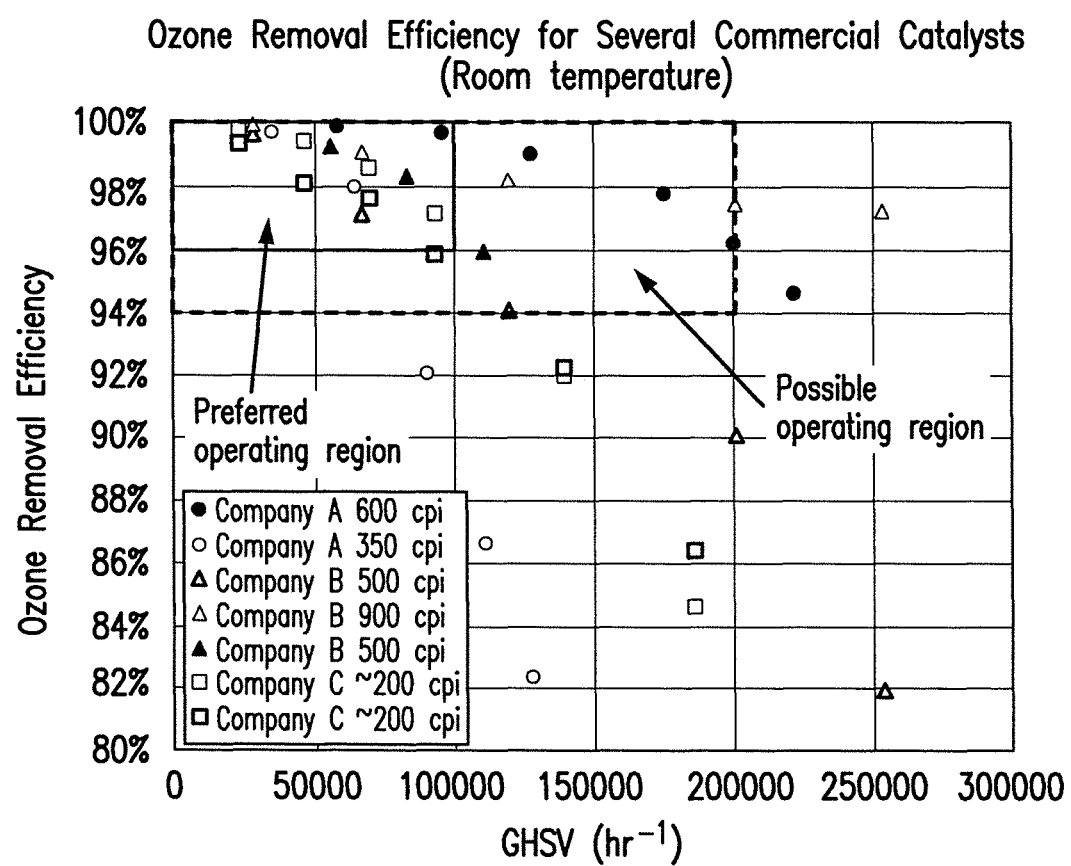
FIG. 14 shows the ozone reduction performance of several catalyst formulations on different substrate geometries at a range of space velocities.

FIG. 14 is a graph that shows the possible and preferred operating region of the catalysts for ozone operation. High ozone removal efficiencies are achieved with space velocities below 200,000 hr-1 and preferably below 100,000 hr-1. The ozone removal efficiencies are uniformly above 98% at space velocities below 30,000 hr-1.

It is to be understood that the disclosed subject matter is not limited in its application to the details of construction and to the arrangements of the components set forth in the description or illustrated in the drawings. The disclosed subject matter is capable of other embodiments and of being practiced and carried out in various ways. Also, it is to be understood that the phraseology and terminology employed herein are for the purpose of illustration and should not be regarded as limiting.

As such, those skilled in the art will appreciate that the conception, upon which this disclosure is based, may readily be utilized as a basis for the designing of other structures, methods, and systems for carrying out the several purposes of the disclosed subject matter. It is important, therefore, that the claims be regarded as including such equivalent constructions insofar as they do not depart from the spirit and scope of the disclosed subject matter.

For example, the term "air" is used in general in this document and it can be interpreted to include both natural air and/or any gaseous or vaporous matter.

With the method and apparatus according to different embodiments of this invention, the modularity of the system can be arranged so that a manufacturer can add or remove elements into a common platform to achieve different products.

The invention claimed is:

1. An apparatus for treating air, comprising:
a housing with an air inlet positioned at a first end of the housing and an air outlet positioned at a second end of the housing opposite the first end, the air inlet and the air outlet being positioned on a same lateral side of the housing, the housing enclosing an air treatment zone and an ozone removal zone, wherein the ozone removal zone is positioned downstream of the air treatment zone with respect to a flow direction of the air being treated;
a first UV light in the air treatment zone and arranged to generate ozone;
a bulb reflector and a UV baffle positioned between the first UV light and the air inlet and arranged to prevent UV illumination from exiting the first end of the housing, the bulb reflector having a concave shape that faces the first UV light and a convex shape that faces the UV baffle, the UV baffle having a curved surface that matches a portion of the convex shape of the bulb reflector;
a grease filter in the air treatment zone and arranged to remove grease and smoke from the air being treated, the grease filter being arranged downstream of the first UV light and to receive UV illumination from the first UV light;
a plurality of first catalyst layers downstream of the grease filter in the air treatment zone and including a first catalyst material, the plurality of first catalyst layers being spaced from each other and arranged to oxidize organic and/or inorganic compounds;
a plurality of second catalyst layers in the ozone removal zone and including a second catalyst material that is different from the first catalyst material, wherein the second catalyst material is arranged to remove ozone from the air being treated; and
a fan downstream of the plurality of second catalyst layers and arranged to move air to be treated into the air inlet, through the air treatment zone and ozone removal zone and out the air outlet.

2. The apparatus of claim 1, further comprising an ozone generator and/or an ultraviolet source disposed downstream of, or between at least two of the first catalyst layers.

3. The apparatus of claim 2, wherein the ozone generator and/or ultraviolet source is downstream of the plurality of first catalyst layers and is configured to promote oxidation of chemical contaminants via the first catalyst material and/or to clean at least one of the plurality of first catalyst layers.

4. The apparatus of claim 1, further comprising a second UV light in the ozone removal zone and positioned between at least two of the second catalyst layers, the second UV light arranged to clean the at least two second catalyst layers.

5. The apparatus of claim 1, a heater within the air treatment zone and in combination with the first catalyst layer.

6. The apparatus of claim 1, wherein each of the first and second catalyst materials comprises manganese.

7. The apparatus of claim 6, further comprising a first ozone generator upstream of the plurality of first catalyst layers, and a second ozone generator and/or an ultraviolet source disposed downstream of the plurality of first catalyst layers.

8. The apparatus of claim 1, further comprising spacers between adjacent first or second catalyst layers for preventing or disrupting a linear air flow through the catalyst layers.

9. The apparatus of claim 1, wherein the apparatus comprises is adapted to operate in a self-clean mode for the grease filter, wherein the self-clean mode includes direct contact of the grease filter with ozone and/or ultraviolet light.

10. The apparatus of claim 9, wherein the self-clean mode includes operating the fan at a lower flow rate than an air cleaning mode, operating the first UV light to deliver ozone to the plurality of first and second catalyst layers at concentrations higher than delivered in the air cleaning mode; and operating the first UV light to apply ultraviolet light into the plurality of first and second catalyst layers.

11. The apparatus of claim 1, wherein the apparatus is controlled by outputs from a surrounding environment, selected from environment sensors and/or operation of fans, motors, or appliances, separate and independent from the apparatus.

12. The apparatus of claim 1, further comprising an adsorbent layer upstream of the plurality of first catalyst layers.

13. The apparatus of claim 1, wherein the housing comprises module attachments, and further comprising a first attachable module including an ozone generator, and a second attachable module including the plurality of first and/or second catalyst layers.

14. An apparatus for treating air, comprising:
a housing with an air inlet positioned at a first end of the housing and an air outlet positioned at a second end of the housing opposite the first end, the air inlet and the air outlet being positioned on a same lateral side of the housing, the housing enclosing an air treatment zone and an ozone removal zone, wherein the ozone removal zone is positioned downstream of the air treatment zone with respect to a flow direction of the air flow being treated;
a first ultraviolet source within the air treatment zone;
a bulb reflector and a UV baffle positioned between the first ultraviolet source and the air inlet and arranged to prevent UV illumination from exiting the first end of the housing, the bulb reflector having a concave shape that faces the first ultraviolet source and a convex shape that faces the UV baffle, the UV baffle having first and second portions at opposed walls of the housing, each of the first and second portions having a curved surface that matches a portion of the convex shape of the bulb reflector;
a grease filter in the air treatment zone and arranged to remove grease and smoke from the air being treated, the grease filter being arranged downstream of the first ultraviolet source and to receive UV illumination from the first ultraviolet source;
a pair of first catalyst layers separated by an air space and each extending across the air treatment zone, and each including a first catalyst material; and a second catalyst layer extending across the ozone removal zone, the second catalyst layer including a second catalyst material that is different from the first catalyst material.

15. The apparatus of claim 14, each of the first and second catalyst materials comprises manganese.

16. An apparatus for treating air, comprising:
a housing with an air inlet positioned at a first end of the housing and an air outlet positioned at a second end of the housing opposite the first end, the air inlet and the air outlet being positioned on a same lateral side of the housing, the housing enclosing an air treatment zone and an ozone removal zone, wherein the ozone removal zone is positioned downstream of the air treatment zone with respect to a flow direction of the air flow being treated;
a first UV light in the air treatment zone and arranged to generate ozone;
a bulb reflector and a UV baffle positioned between the first UV light and the air inlet and arranged to prevent UV illumination from exiting the first end of the housing, the bulb reflector having a concave shape that faces the first UV light and a convex shape that faces the UV baffle, the UV baffle having a curved surface that matches a portion of the convex shape of the bulb reflector;
a plurality of first catalyst layers each spaced apart from each other and extending across the air treatment zone, and each including a first catalyst material;
a plurality of second catalyst layers extending across the ozone removal zone, each spaced apart from each other and the first catalyst layers, the second catalyst layers each including a second catalyst material that is different from the first catalyst material, wherein each of the first and second catalyst materials comprises manganese;
an ozone and/or ultraviolet source disposed within an air flow space between the first and second catalyst layers or between the second catalyst layers and a downstream further catalyst layer, wherein the further catalyst layer comprises the first catalyst material or the second catalyst material; and
a heater disposed between the first UV light and the plurality of first catalyst layers.

17. The apparatus of claim 16, further comprising a particulate filter between the first UV light and the heater.

18. The apparatus of claim 16, wherein the heater is configured to increase a temperature of air through the first catalyst material.

19. The apparatus of claim 14, further comprising a heater disposed downstream of the first ultraviolet source and upstream of the pair of first catalyst layers.

20. The apparatus of claim 1, wherein the UV baffle includes first and second portions extending inwardly from opposed walls of the housing, each of the first and second portions including a panel that extends inwardly and upwardly from a respective wall of the housing to a concave curved surface that extends upwardly and outwardly to the respective wall.

21. The apparatus of claim 1, wherein the air inlet and the air outlet are arranged so that air enters the air inlet in a horizontal direction and turns upwardly to flow towards the air treatment zone and air exits the ozone removal zone upwardly and turns horizontally to exit the air outlet.

22. The apparatus of claim 1, further comprising a controller arranged to operate the apparatus in a self-clean mode in which the first UV light and the fan are operated to generate ozone in the air treatment zone at a self-clean level of 500 ppb to 2 ppm and to provide a self-clean space velocity in the catalyst of less than 100,000/hr to clean the grease filter and the plurality of first catalyst layers of organic material, and in a normal mode in which the first UV light and fan are operated to generate ozone in the air treatment zone at a normal level that is less than the self-clean level and a normal space velocity that is greater than the self-clean space velocity.

23. The apparatus of claim 1, further comprising a second UV light in the ozone removal zone and positioned between at least two of the second catalyst layers, the second UV light arranged to clean the at least two second catalyst layers.

* * * * *

UNITED STATES PATENT AND TRADEMARK OFFICE
CERTIFICATE OF CORRECTION

PATENT NO.         : 10,933,158 B2
APPLICATION NO.    : 16/268128
DATED              : March 2, 2021
INVENTOR(S)        : Karen Benedek et al.

Page 1 of 1

It is certified that error appears in the above-identified patent and that said Letters Patent is hereby corrected as shown below:

In the Claims

At Column 22, Claim 9, Lines 14-15, "apparatus comprises is adapted" should read -- apparatus is adapted --

Signed and Sealed this
Sixth Day of April, 2021

Drew Hirshfeld
*Performing the Functions and Duties of the
Under Secretary of Commerce for Intellectual Property and
Director of the United States Patent and Trademark Office*